US009498116B2

(12) United States Patent
Shibutani et al.

(10) Patent No.: US 9,498,116 B2
(45) Date of Patent: Nov. 22, 2016

(54) OPHTHALMOLOGIC APPARATUS

(71) Applicant: KABUSHIKI KAISHA TOPCON, Itabashi-ku (JP)

(72) Inventors: Masahiro Shibutani, Kawaguchi (JP); Hiroyuki Aoki, Saitama (JP)

(73) Assignee: KABUSHIKI KAISHA TOPCON, Itabashi-ku (JP)

(*) Notice: Subject to any disclaimer, the term of this patent is extended or adjusted under 35 U.S.C. 154(b) by 0 days.

(21) Appl. No.: 14/911,923

(22) PCT Filed: Jul. 29, 2014

(86) PCT No.: PCT/JP2014/069923
§ 371 (c)(1),
(2) Date: Feb. 12, 2016

(87) PCT Pub. No.: WO2015/029675
PCT Pub. Date: Mar. 5, 2015

(65) Prior Publication Data
US 2016/0198940 A1 Jul. 14, 2016

(30) Foreign Application Priority Data

Aug. 28, 2013 (JP) ................................. 2013-177388

(51) Int. Cl.
*A61B 3/14* (2006.01)
*A61B 3/00* (2006.01)
(Continued)

(52) U.S. Cl.
CPC ............. *A61B 3/0025* (2013.01); *A61B 3/102* (2013.01); *A61B 3/113* (2013.01); *A61B 3/1225* (2013.01); *A61B 3/145* (2013.01)

(58) Field of Classification Search
USPC ........ 351/200, 203, 205, 206, 209–211, 222, 351/223, 237, 243–246
See application file for complete search history.

(56) References Cited

U.S. PATENT DOCUMENTS

| 6,824,269 B2 * | 11/2004 | Takeuchi ................. A61B 3/12 351/211 |
| 2013/0222566 A1 * | 8/2013 | Murase .............. G01B 9/02076 348/78 |

FOREIGN PATENT DOCUMENTS

| JP | 2011-135933 A | 7/2011 |
| JP | 2013-154121 A | 8/2013 |

OTHER PUBLICATIONS

International Search Report mailed Sep. 9, 2014, in PCT/JP2014/069923, filed Jul. 29, 2014.
(Continued)

*Primary Examiner* — Joseph P Martinez
*Assistant Examiner* — Brandi Thomas
(74) *Attorney, Agent, or Firm* — Oblon, McClelland, Maier & Neustadt, L.L.P.

(57) ABSTRACT

An ophthalmologic apparatus of an embodiment includes an optical system, a rotational movement amount calculator, a registration unit, a parallel movement amount calculator, a driver, and a controller. The optical system is used to capture a moving image of a subject's eye. The rotational movement amount calculator calculates a rotational movement amount between a first image and a second image included in the moving image. The registration unit performs registration between the first image and the second image in the rotation direction based on the rotational movement amount. The parallel movement amount calculator performs a phase only correlation process on the first image and the second image registered by the registration unit to calculate a parallel movement amount between the first image and the second image. The driver moves the optical system. The controller controls the driver based on the parallel movement amount.

15 Claims, 21 Drawing Sheets

(51) Int. Cl.
*A61B 3/10* (2006.01)
*A61B 3/113* (2006.01)
*A61B 3/12* (2006.01)

(56) References Cited

OTHER PUBLICATIONS

Nemoto, Yusuke, Katayama, Kaoru, "Retrieving large multidimensional data using phase-only correlation", The Third Forum on Data Engineering and Information Management Ronbunshu, Jul. 27, 2011, (retrieval date Aug. 27, 2014), Internet <URL: http://db-event.jpn.org/deim2011/proceedings/pds/d6-.1.pdf, 8 pages.
Sei Nagashima, et al., "Improving Performance for Subpixel Image Matching Based on Phase-Only Correlation" The Society of Instrument and Control Engineers Tohoku Branch, 218th Research meeting, Oct. 19, 2004, pp. 1-10 (with English language translation).
Yusuke Nemoto, et al., "Retrieving large multidimensional data using phase-only correlation" The Third Forum on Data Engineering and Information Management Ronbunshu, 2011, 16 pages. (reference previously filed, submitting English translation only).

\* cited by examiner

OPHTHALMOLOGIC APPARATUS

TECHNICAL FIELD

Embodiments described herein relate generally to an ophthalmologic apparatus that captures an image of a subject's eye.

BACKGROUND ART

Examples of ophthalmologic apparatuses for capturing an image of the fundus or the anterior segment of the subject's eye include an apparatus using optical coherence tomography (OCT), a fundus camera, a scanning laser ophthalmoscope (SLO), a slit lamp, and the like. Among them, OCT has been drawing attention. OCT creates an image representing the exterior structure, interior structure, or the like of an object to be measured using light beams from a laser light source or the like. Unlike X-ray computed tomography (CT), OCT is not invasive on the human body, and therefore is expected to be applied to the medical field and the biological field, in particular. For example, in the ophthalmological field, apparatuses for forming images of the fundus oculi or the cornea have been in practical use.

Patent Document 1 discloses a device using Fourier-domain OCT or frequency-domain OCT. This device irradiates an object to be measured with a beam of low-coherence light, and superimposes the light reflected from the object on reference light to generate interference light. The device then obtains the spectral intensity distribution of the interference light, and applies Fourier transform thereto to acquire an image of the morphology of the object to be measured in the depth direction (z direction). The device includes a galvanometer mirror configured to scan a light beam (signal light) in a direction (x direction) perpendicular to the z direction, thereby forming an image of a desired area of the object to be measured. The image formed by the device is a two-dimensional tomographic image in the depth direction (z direction), taken along the scanning direction (x direction) of the light beam. This technique is also called "spectral-domain".

Patent Document 2 discloses a technology, in which signal light is scanned in the horizontal direction (x direction) and the vertical direction (y direction) to thereby form a plurality of two-dimensional tomographic images in the horizontal direction. Based on the tomographic images, three-dimensional tomographic information is acquired for a measurement range. As the three-dimensional imaging, for example, there are a method of displaying a plurality of tomographic images arranged in the vertical direction (referred to as "stack data", etc.), a method of performing rendering on volume data (voxel data) generated based on the stack data to thereby form a three-dimensional image, and the like.

Patent Documents 3 and 4 disclose OCT devices of other types. Patent Document 3 discloses an OCT device, which scans (sweeps) the wavelengths of light irradiated to the object to be measured, and sequentially detects interference light obtained by superimposing reflected light of each wavelength on reference light to acquire spectral intensity distribution. The device applies Fourier transform to the spectral intensity distribution to form an image of the morphology of the object to be measured. Such an OCT device is called swept source OCT. The swept source OCT is a type of Fourier-domain OCT.

Patent Document 4 discloses an OCT device, which irradiates light beams having a predetermined diameter to an object to be measured, and analyzes the component of interference light obtained by superimposing the reflected light on reference light. Thereby, the device forms an image of the object to be measured in a cross-section perpendicular to the traveling direction of the light. Such an OCT device is called full-field OCT or en-face OCT.

Patent Document 5 discloses a configuration in which OCT is applied to the ophthalmologic field. Incidentally, before the application of OCT, a fundus camera, a slit lamp, SLO, or the like has been used as a device for observing the subject's eye (see, for example, Patent Documents 6, 7, and 8). The fundus camera is a device that irradiates the subject's eye with illumination light and receives the light reflected from the fundus to thereby capture an image of the fundus. The slit lamp is a device that cuts an optical section of the cornea using a slit light to thereby acquire an image of the cross-section of the cornea. The SLO is a device that scans the fundus with a laser beam, and detects the reflected light with a high-sensitivity element such as a photomultiplier tube for imaging the morphology of the fundus surface.

The devices using OCT offer advantages with respect to the fundus camera in that they can acquire high-resolution images, and also that they can obtain tomographic images as well as three-dimensional images.

As described above, the devices using OCT can be used for the observation of different parts of the subject's eye, and are capable of acquiring high-resolution images. Therefore, the OCT devices have been used in diagnosing a variety of ophthalmologic diseases.

Among those using OCT, there has been a known ophthalmologic apparatus configured to capture a high-resolution image regardless of the involuntary eye movement during fixation (flicks) of the subject's eye (see, for example, Patent Document 9). Besides, there has been a known method for obtaining misregistration between two images using a phase only correlation function (see, for example, Patent Document 10). For more information regarding the phase only correlation function, reference may be made to, for example, Non-Patent Document 1.

[Patent Document 1] Japanese Unexamined Patent Application Publication No. Hei 11-325849
[Patent Document 2] Japanese Unexamined Patent Application Publication No. 2002-139421
[Patent Document 3] Japanese Unexamined Patent Application Publication No. 2007-24677
[Patent Document 4] Japanese Unexamined Patent Application Publication No. 2006-153838
[Patent Document 5] Japanese Unexamined Patent Application Publication No. 2008-73099
[Patent Document 6] Japanese Unexamined Patent Application Publication No. Hei 9-276232
[Patent Document 7] Japanese Unexamined Patent Application Publication No. 2008-259544
[Patent Document 8] Japanese Unexamined Patent Application Publication No. 2009-11381
[Patent Document 9] Japanese Unexamined Patent Application Publication No. 2011-212103
[Patent Document 10] Japanese Unexamined Patent Application Publication No. 2010-110391

Non-Patent Documents

[Non-Patent Document 1] Sei Nagashima, Takafumi Aoki, Tatsuo Higuchi, Koji Kobayashi, "Improving Performance for Subpixel Image Matching Based on Phase only correlation", The Society of Instrument and Control Engineers Tohoku Branch, 218th Research meeting (2004.10.9), Document No. 218-15

SUMMARY OF THE INVENTION

Problems to be Solved by the Invention

For the ophthalmologic apparatus, tracking is an important technique to obtain a high-definition moving image regardless of the eye movement of the subject. The ophthalmologic apparatus that performs tracking is desirably configured to be able to detect a slight misregistration as possible, and correct the misregistration based on the slight amount of the misregistration. However, a simple application of the phase only correlation function as disclosed in Non-Patent Document 1 cannot always detect a slight misregistration accurately.

The present invention has been made to solve the above problems, and therefore one object thereof is to provide a technology for detecting a slight misregistration, which can be applied to tracking for a moving image.

Means of Solving the Problems

An embodiment is an ophthalmologic apparatus including: an optical system configured to capture a moving image of a subject's eye; a rotational movement amount calculator configured to calculate a rotational movement amount between a first image and a second image included in the moving image acquired by the optical system; a registration unit configured to perform registration between the first image and the second image in a rotation direction based on the rotational movement amount calculated by the rotational movement amount calculator; a parallel movement amount calculator configured to perform a phase only correlation process on the first image and the second image registered by the registration unit to calculate a parallel movement amount between the first image and the second image; a driver configured to move the optical system; and a controller configured to control the driver based on the parallel movement amount calculated by the parallel movement amount calculator.

According to the present invention, a rotational movement amount between two images is calculated, and, after they are registered based on the amount calculated, a parallel movement amount between them is calculated. Thereby, even a slight misregistration can be detected accurately. Thus, it is possible to provide a technology applicable to tracking for a moving image.

MODES FOR CARRYING OUT THE INVENTION

Figure 1:
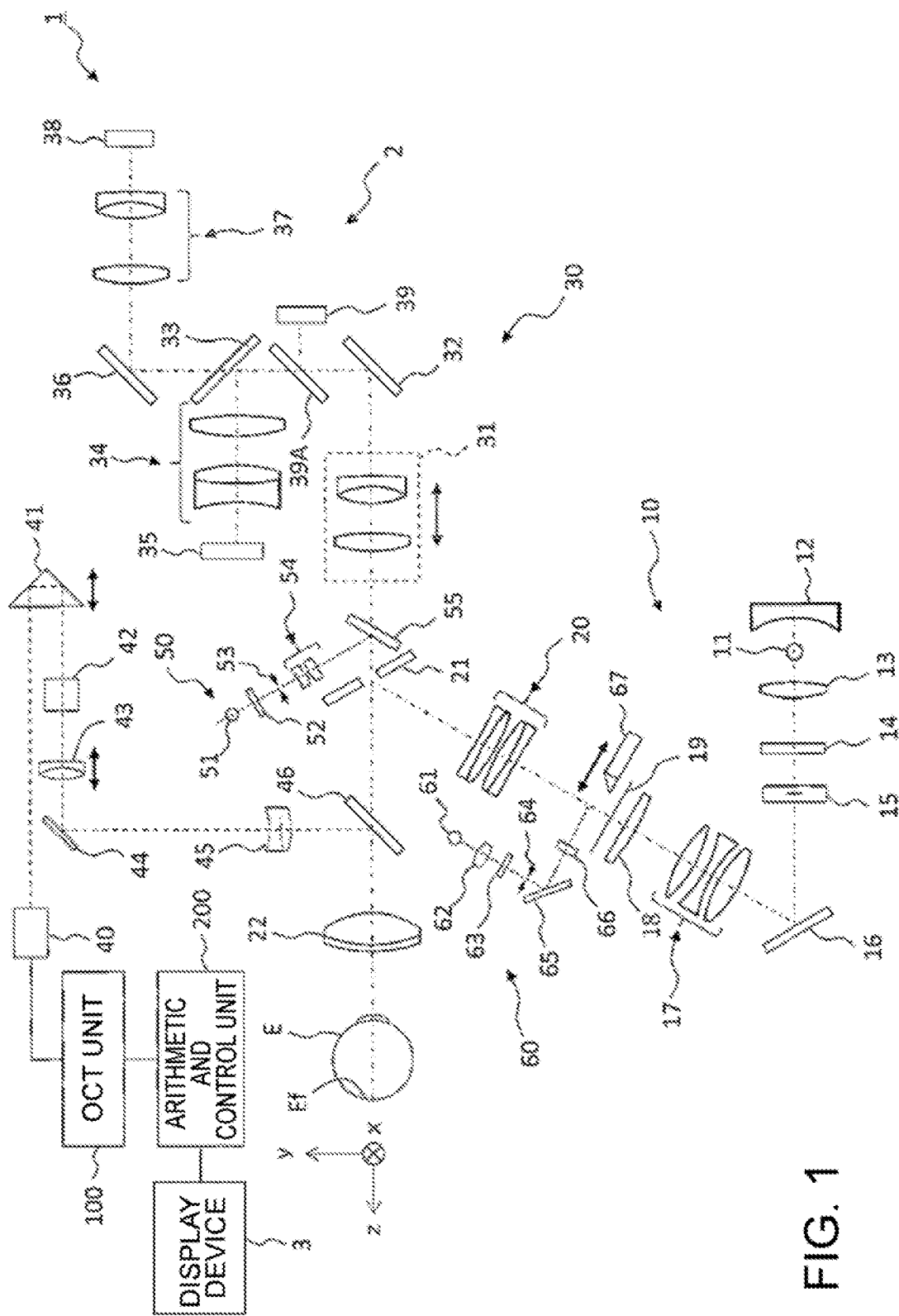
FIG. 1 is a schematic diagram illustrating an example of the configuration of an ophthalmologic apparatus according to an embodiment.

Referring now to the drawings, a detailed description is given of an ophthalmologic apparatus according to illustrative embodiments. The ophthalmologic apparatus of an embodiment creates a tomographic image, a three-dimensional image and the like of the fundus of an eye using OCT imaging. Hereinafter, the image acquired through OCT may sometimes be referred to as "OCT image". In addition, measurement for forming the OCT image may sometimes be referred to as "OCT measurement". The contents of the documents cited herein may be incorporated by reference into the embodiments as appropriate.

While the following embodiment is described as using spectral-domain OCT, the embodiments can be applied to ophthalmologic apparatuses using other types of OCT (e.g., swept source OCT). Further, an apparatus that combines the functions of an OCT device and a fundus camera is explained in the following embodiments; however, the OCT device having a configuration of the embodiments can be applied to other photographing devices than the fundus camera, such as an SLO, a slit lamp, an ophthalmic surgical microscope, and the like. In addition, the embodiments can also be applied to an apparatus having the function of the OCT device only.

First Embodiment

Configuration

Figure 2:
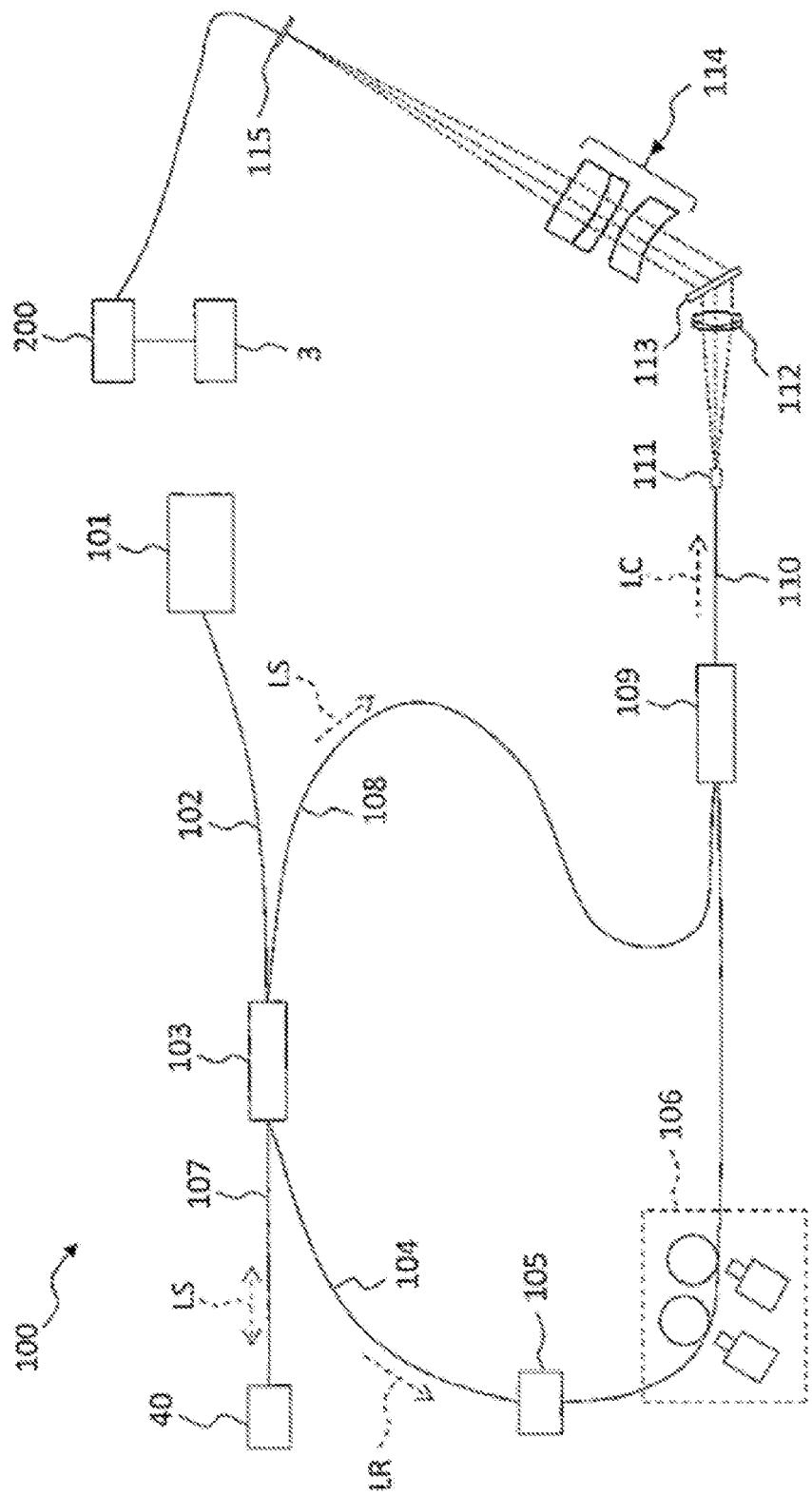
FIG. 2 is a schematic diagram illustrating an example of the configuration of the ophthalmologic apparatus of the embodiment.

As illustrated in FIGS. 1 and 2, an ophthalmologic apparatus 1 includes a fundus camera unit 2, an OCT unit 100, and an arithmetic and control unit 200. The fundus camera unit 2 has almost the same optical system as a conventional fundus camera. The OCT unit 100 is provided with an optical system for obtaining an OCT image of a fundus. The arithmetic and control unit 200 is provided with a computer that performs various arithmetic processes, control processes, and the like.

[Fundus Camera Unit]

The fundus camera unit 2 illustrated in FIG. 1 is provided with an optical system for forming a two-dimensional image (fundus image) representing the surface morphology of the fundus Ef of the subject's eye E. Fundus images include observation images, photographed images, and the like. The observation image is, for example, a monochrome moving image formed at a predetermined frame rate using near-infrared light. The photographed image may be, for example, a color image captured by flashing visible light or a monochrome still image using near-infrared light or visible light as illumination light. The fundus camera unit 2 may be configured to be capable of acquiring other types of images such as a fluorescein angiography image, an indocyanine green fluorescent image, and a fundus autofluorescent image. Incidentally, the observation image corresponds to an example of "moving image".

The fundus camera unit 2 is provided with a jaw holder and a forehead rest for supporting the face of the subject. The fundus camera unit 2 is also provided with an illumination optical system 10 and an imaging optical system 30. The illumination optical system 10 irradiates illumination light to the fundus Ef. The imaging optical system 30 guides the illumination light reflected from the fundus to imaging devices (CCD image sensors 35 and 38, sometimes simply referred to as "CCD"). Further, the imaging optical system 30 guides signal light coming from the OCT unit 100 to the fundus Ef, and guides the signal light having passed through the fundus Ef to the OCT unit 100. Incidentally, the illumination optical system 10 and the imaging optical system 30 of the fundus camera unit 2 correspond to an example of "optical system" used to capture a moving image of a subject's eye.

An observation light source 11 of the illumination optical system 10 includes, for example, a halogen lamp. The light (observation illumination light) output from the observation light source 11 is reflected by a reflection mirror 12 having a curved reflective surface, and becomes near-infrared light after passing through a visible cut filter 14 via a condenser lens 13. Further, the observation illumination light is once converged near an imaging light source 15, reflected by a mirror 16, and passes through relay lenses 17 and 18, a diaphragm 19, and a relay lens 20. Then, the observation illumination light is reflected on the peripheral part (the surrounding region of an aperture part) of an aperture mirror 21, penetrates a dichroic mirror 46, and refracted by the objective lens 22, thereby illuminating the fundus Ef. Note that a light emitting diode (LED) may be used as the observation light source.

The observation illumination light reflected from the fundus is refracted by the objective lens 22, penetrates the dichroic mirror 46, passes through the aperture part formed in the center region of the aperture mirror 21, passes through a dichroic mirror 55, travels through a focusing lens 31, and is reflected by a mirror 32. Further, the fundus reflection light passes through a half mirror 39A, is reflected by a dichroic mirror 33, and forms an image on the light receiving surface of the CCD image sensor 35 by a condenser lens 34. The CCD image sensor 35 detects, for example, the fundus reflection light at a predetermined frame rate. An image (observation image) based on the fundus reflection light detected by the CCD image sensor 35 is displayed on a display device 3. Note that when the imaging optical system 30 is focused on the anterior eye segment, an observation image of the anterior eye segment of the subject's eye E is displayed.

The imaging light source 15 is formed of, for example, a xenon lamp. The light (imaging illumination light) output from the imaging light source 15 is irradiated to the fundus Ef via a route as with the observation illumination light. The imaging illumination light reflected from the fundus is guided to the dichroic mirror 33 via the same route as that of the observation illumination light, passes through the dichroic mirror 33, is reflected by a mirror 36, and forms an image on the light receiving surface of the CCD image sensor 38 by a condenser lens 37. An image (photographed image) based on the fundus reflection light detected by the CCD image sensor 38 is displayed on the display device 3. Note that the same device or different devices may be used as the display device 3 for displaying an observation image and the display device 3 for displaying a photographed image. Besides, when similar photographing is performed by illuminating the subject's eye E with infrared light, an infrared photographed image is displayed. Further, an LED may be used as the imaging light source.

A liquid crystal display (LCD) 39 displays a fixation target or a visual target for measuring visual acuity. The fixation target is a visual target for fixating the subject's eye E, and is used on the occasion of photographing of a fundus or OCT measurement.

Part of the light output from the LCD 39 is reflected by the half mirror 39A, reflected by the mirror 32, travels through the focusing lens 31 and the dichroic mirror 55, passes through the aperture part of the aperture mirror 21, penetrates the dichroic mirror 46, and is refracted by the objective lens 22, thereby being projected onto the fundus Ef.

By changing a display position of the fixation target on the screen of the LCD 39, the fixation position of the subject's eye E can be changed. Examples of the fixation position of the subject's eye E include, as in conventional fundus cameras, a position for acquiring an image centered on the macula of the fundus Ef, a position for acquiring an image centered on the optic papilla, a position for acquiring an image centered on the fundus center between the macula and the optic papilla, and the like. Further, the display position of the fixation target may be arbitrarily changed.

Further, as with conventional fundus cameras, the fundus camera unit 2 is provided with an alignment optical system 50 and a focus optical system 60. The alignment optical system 50 generates a target (alignment indicator) for position matching (alignment) of the optical system with respect to the subject's eye E. The focus optical system 60 generates a target (split target) for adjusting the focus with respect to the subject's eye E.

The light (alignment light) output from an LED 51 of the alignment optical system 50 travels through diaphragms 52 and 53 and a relay lens 54, is reflected by the dichroic mirror 55, passes through the aperture part of the aperture mirror 21, penetrates the dichroic mirror 46, and is projected onto the cornea of the subject's eye E by the objective lens 22.

The alignment light reflected from the cornea travels through the objective lens 22, the dichroic mirror 46 and the abovementioned aperture part, and part of the cornea reflection light penetrates the dichroic mirror 55, passes through the focusing lens 31, is reflected by the mirror 32, penetrates the half mirror 39A, is reflected by the dichroic mirror 33, and is projected onto the light receiving surface of the CCD image sensor 35 by the condenser lens 34. An image (alignment indicator) captured by the CCD image sensor 35 is displayed on the display device 3 together with the observation image. A user conducts alignment by the same operation as performed on a conventional fundus camera. Instead, alignment may be performed in such a way that the arithmetic and control unit 200 analyzes the position of the alignment indicator and moves the optical system (automatic alignment).

To conduct focus adjustment, the reflective surface of a reflection rod 67 is arranged in a slanted position on the optical path of the illumination optical system 10. The light (focus light) output from an LED 61 of the focus optical system 60 passes through a relay lens 62, is split into two light fluxes by a split target plate 63, passes through a two-hole diaphragm 64, is reflected by a mirror 65, and is reflected after an image is once formed on the reflective surface of the reflection rod 67 by a condenser lens 66. Further, the focus light travels through the relay lens 20, is reflected by the aperture mirror 21, penetrates the dichroic mirror 46, and is refracted by the objective lens 22, thereby being projected onto the fundus Ef.

The focus light reflected from the fundus passes through the same route as the alignment light reflected from the cornea and is detected by the CCD image sensor 35. An image (split target) captured by the CCD image sensor 35 is displayed on the display device 3 together with an observation image. As in the conventional case, the arithmetic and control unit 200 analyzes the position of the split target, and moves the focusing lens 31 and the focus optical system 60 for focusing (automatic focusing). The user may perform the focusing manually while visually checking the split target.

The dichroic mirror 46 branches an optical path for OCT measurement from an optical path for fundus photography. The dichroic mirror 46 reflects light of wavelengths used in OCT measurement, and transmits light for fundus photography. This optical path for OCT measurement is provided with, in order from the OCT unit 100 side, a collimator lens unit 40, an optical path length changing unit 41, a galvano-scanner 42, a focusing lens 43, a mirror 44, and a relay lens 45.

The optical path length changing unit 41 is movable in a direction indicated by the arrow in FIG. 1, thereby changing the length of the optical path for OCT measurement. This change in the optical path length is used for correcting the optical path according to the axial length of the subject's eye E, adjusting the interference state, and the like. The optical path length changing unit 41 includes, for example, a corner cube and a mechanism for moving it.

The galvano-scanner 42 changes the travelling direction of light (signal light LS) travelling through the optical path for OCT measurement. Thereby, the fundus Ef may be scanned with the signal light LS. The galvano-scanner 42 includes, for example, a galvanometer mirror for scanning the signal light LS in the x direction, a galvanometer mirror for scanning the light in the y direction, and a mechanism for independently driving them. Accordingly, the signal light LS may be scanned in any direction on the xy plane.

[OCT Unit]

An example of the configuration of the OCT unit 100 is described with reference to FIG. 2. The OCT unit 100 is provided with an optical system for acquiring an OCT image of the fundus Ef. The optical system has a similar configuration to that of a conventional spectral-domain OCT. That is, the optical system is configured to split low-coherence light into reference light and signal light, make the signal light having passed through the fundus Ef and the reference light having travelled through a reference optical path interfere with each other to generate interference light, and detect the spectral component of this interference light. This detection result (detection signal) is sent to the arithmetic and control unit 200.

Note that, in the case of swept source OCT, a wavelength sweeping light source is provided instead of a light source that outputs low-coherence light, while an optical element for spectrally decomposing interference light is not provided. Generally, regarding the configuration of the OCT unit 100, known technologies may be applied according to the type of OCT.

A light source unit 101 outputs broadband low-coherence light L0. The low-coherence light L0 includes, for example, near-infrared wavelengths (approximately 800 nm to 900 nm), and has a temporal coherence length of around several tens of micrometers. Note that, wavelengths not visible to the human eye, such as, for example, near-infrared light with a central wavelength of around 1040 nm to 1060 nm may be used as the low-coherence light L0.

The light source unit 101 includes a light output device, such as a super luminescent diode (SLD), an LED, a semiconductor optical amplifier (SOA), or the like.

The low coherence light L0 output from the light source unit 101 is guided to a fiber coupler 103 by an optical fiber 102 and split into signal light LS and reference light LR.

The reference light LR is guided by an optical fiber 104 and arrives at an optical attenuator 105. The optical attenuator 105 automatically adjusts the amount of the reference light LR guided by the optical fiber 104 under the control of the arithmetic and control unit 200 using a known technology. The reference light LR in the light amount having adjusted by the optical attenuator 105 is guided by the optical fiber 104 and arrives at a polarization adjuster (polarization controller) 106. The polarization adjuster 106 is a device that, by applying external stress to the looped optical fiber 104, adjusts the polarization condition of the reference light LR guided in the optical fiber 104. Note that the configuration of the polarization adjuster 106 is not limited to this and any known technologies may be used. The reference light LR with polarization condition adjusted by the polarization adjuster 106 arrives at a fiber coupler 109.

The signal light LS generated by the fiber coupler 103 is guided by an optical fiber 107 and collimated into a parallel light flux by the collimator lens unit 40. Further, the signal light LS arrives at the dichroic mirror 46 via the optical path length changing unit 41, the galvano-scanner 42, the focusing lens 43, the mirror 44, and the relay lens 45. Subsequently, the signal light LS is reflected by the dichroic mirror 46, refracted by the objective lens 22, and projected onto the fundus Ef. The signal light LS is scattered (and reflected) at various depth positions of the fundus Ef. Back-scattered light of the signal light LS from the fundus Ef reversely advances along the same path as the outward path and is guided to the fiber coupler 103, thereby arriving at the fiber coupler 109 through an optical fiber 108.

The fiber coupler 109 causes the back-scattered light of the signal light LS and the reference light LR having passed through the optical fiber 104 to interfere with each other. Interference light LC thus generated is guided by an optical fiber 110 and output from an exit end 111. Further, the interference light LC is converted to a parallel light flux by a collimator lens 112, spectrally divided (spectrally decomposed) by a diffraction grating 113, converged by a convergence lens 114, and projected onto the light receiving surface of a CCD image sensor 115. Note that although the diffraction grating 113 illustrated in FIG. 2 is of the transmission type, it is possible to use a spectrally decomposing element of any other type, such as a diffraction grating of reflection type.

The CCD image sensor 115 is, for example, a line sensor, and detects the spectral components of the spectrally decomposed interference light LC and converts the components into electric charges. The CCD image sensor 115 accumulates the electric charges to generate a detection signal, and sends the signal to the arithmetic and control unit 200.

Although a Michelson interferometer is employed in the present embodiment, it is possible to employ any type of interferometer such as Mach-Zehnder-type as appropriate. Instead of the CCD image sensor, another type of image sensor, such as a complementary metal-oxide semiconductor (CMOS) image sensor, can be used.

[Arithmetic and Control Unit]

Described blow is the configuration of the arithmetic and control unit 200. The arithmetic and control unit 200 analyzes a detection signal fed from the CCD image sensor 115 to form an OCT image of the fundus Ef. An arithmetic process for this is the same as that of a conventional spectral-domain OCT.

Further, the arithmetic and control unit 200 controls the fundus camera unit 2, the display device 3, and the OCT unit 100. For example, the arithmetic and control unit 200 displays an OCT image of the fundus Ef on the display device 3.

Further, for controlling the fundus camera unit 2, the arithmetic and control unit 200 controls the action of the observation light source 11, the imaging light source 15 and the LEDs 51 and 61, the action of the LCD 39, the movement of the focusing lenses 31 and 43, the movement of the reflection rod 67, the movement of the focus optical system 60, the movement of the optical path length changing unit 41, the action of the galvano-scanner 42, the action of the optical system driver 90 (see FIG. 3) to three-dimensionally move the optical system of the fundus camera unit 2, and the like.

Further, for controlling the OCT unit 100, the arithmetic and control unit 200 controls the action of the light source unit 101, the action of the optical attenuator 105, the action of the polarization adjuster 106, the action of the CCD image sensor 115, and the like.

The arithmetic and control unit 200 includes a microprocessor, RAM, ROM, a hard disk drive, a communication interface, and the like, as with conventional computers. The storage device such as a hard disk drive stores computer programs for controlling the ophthalmologic apparatus 1. The arithmetic and control unit 200 may be provided with various types of circuit boards, such as a circuit board for forming OCT images. The arithmetic and control unit 200 may further include an operation device (input device) such as a keyboard and a mouse, and a display device such as LCD.

The fundus camera unit 2, the display device 3, the OCT unit 100, and the arithmetic and control unit 200 may be integrally provided (i.e., in a single case), or they may be separately provided in two or more cases.

[Control System]

Figure 3:
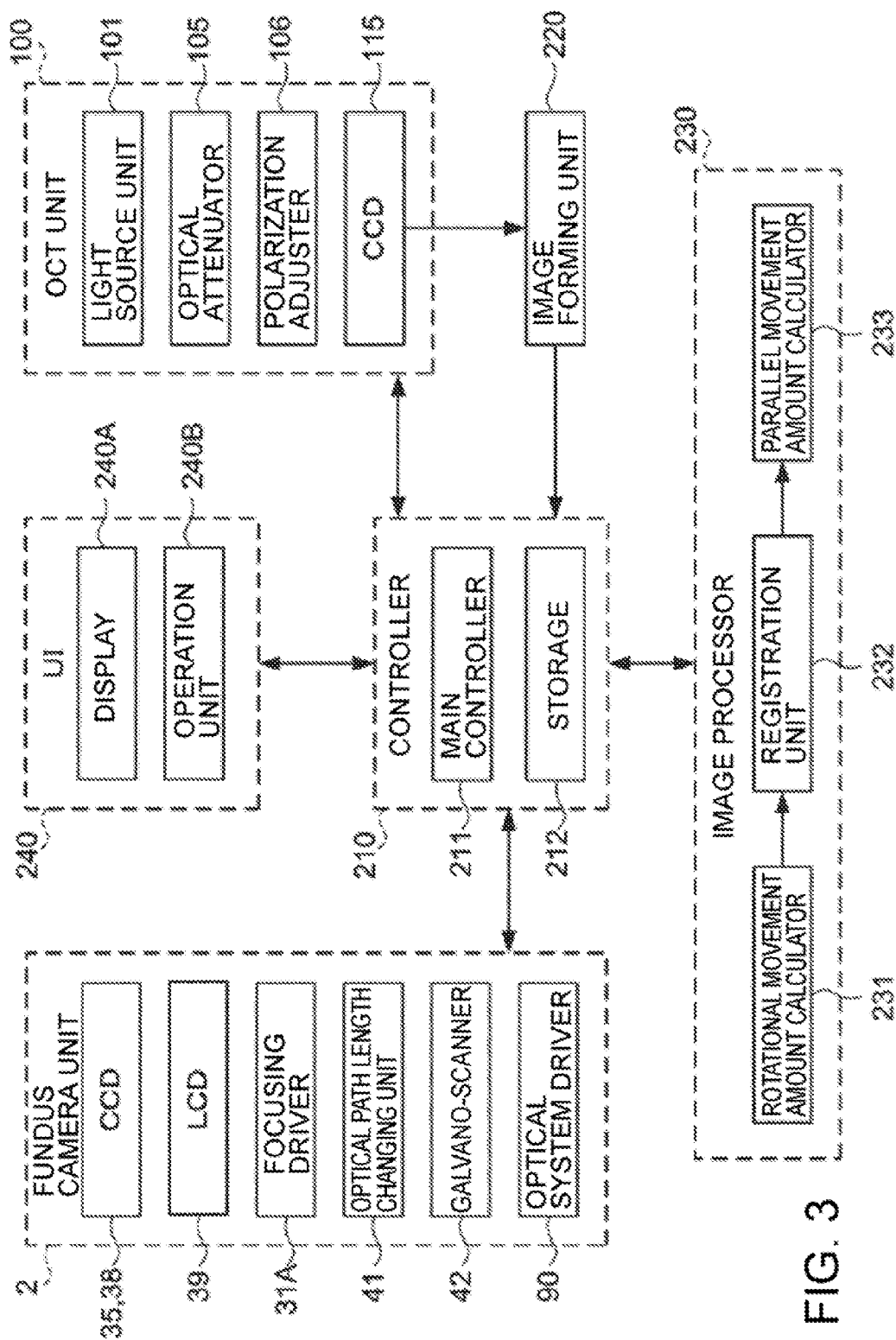
FIG. 3 is a schematic block diagram illustrating an example of the configuration of the ophthalmologic apparatus of the embodiment.

The configuration of a control system of the ophthalmologic apparatus 1 is described with reference to FIG. 3.

(Controller)

The control system of the ophthalmologic apparatus 1 is configured with a controller 210 as a center. The controller 210 includes, for example, the aforementioned microprocessor, RAM, ROM, a hard disk drive, and a communication interface. The controller 210 is provided with a main controller 211 and a storage 212.

(Main Controller)

The main controller 211 performs various types of controls mentioned above. In particular, the main controller 211 controls a focusing driver 31A of the fundus camera unit 2, the optical path length changing unit 41, the galvano-scanner 42, the optical system driver 90, the light source unit 101 of the OCT unit, the optical attenuator 105, and the polarization adjuster 106.

The focusing driver 31A moves the focusing lens 31 in the optical axis direction. This changes the focusing position of the imaging optical system 30. The optical system driver 90 three-dimensionally moves the optical system of the fundus camera unit 2. The optical system driver 90 may rotate the optical system about the optical axis thereof. This control is used in alignment and/or tracking. Here, tracking is to move the optical system of the apparatus according to the eye movement of the subject's eye E. To perform tracking, alignment and focusing are performed in advance. Tracking is a function of causing the position of the optical system of the apparatus to follow the eye movement, thereby maintaining a suitable positional relationship in which alignment and focusing are adjusted.

The main controller 211 performs a process of writing data into the storage 212, and a process of reading out data from the storage 212.

(Storage)

The storage 212 stores various types of data. Examples of the data stored in the storage 212 include, for example, image data of an OCT image, image data of a fundus image, and subject's eye information. The subject's eye information includes information related to a subject such as patient ID and name, information related to the subject's eye such as identification information of left eye/right eye, and the like. The storage 212 further stores various types of programs and data to run the ophthalmologic apparatus 1.

(Image Forming Unit)

An image forming unit 220 forms image data of a tomographic image of the fundus Ef based on a detection signal from the CCD image sensor 115. As with a conventional spectral-domain OCT, this process includes noise removal (noise reduction), filtering, dispersion compensation, fast Fourier transform (FFT), and the like. In the case of another type of OCT device, the image forming unit 220 performs known processes according to the type thereof.

The image forming unit 220 includes, for example, the aforementioned circuit boards. Note that "image data" and the "image" based on this may be treated in the same way in this specification.

(Image Processor)

An image processor 230 performs various types of image processing and analysis on an image formed by the image forming unit 220. For example, the image processor 230 performs various correction processes such as luminance correction of the image. Further, the image processor 230 performs various types of image processing and analysis on an image (fundus image, anterior eye image, etc.) obtained by the fundus camera unit 2.

The image processor 230 performs known image processing such as an interpolation process for interpolating pixels between tomographic images, thereby forming image data of a three-dimensional image of the fundus Ef. The image data of a three-dimensional image refers to image data in which the positions of pixels are defined by a three-dimensional coordinate system. The image data of a three-dimensional image is, for example, image data composed of three-dimensional arrays of voxels. This image data is referred to as volume data, voxel data, or the like. For displaying an image based on the volume data, the image processor 230 performs a rendering process (e.g., volume rendering, maximum intensity projection (MIP), etc.) on the volume data to form image data of a pseudo three-dimensional image taken from a specific view direction. This pseudo three-dimensional image is displayed on a display 240A.

Further, stack data of a plurality of tomographic images may be formed as the image data of a three-dimensional image. The stack data is image data obtained by three-dimensionally arranging the tomographic images obtained along a plurality of scan lines, based on the positional relationship of the scan lines. That is, the stack data is image data obtained by expressing the tomographic images, which are originally defined by their respective two-dimensional coordinate systems, by a three-dimensional coordinate system (i.e., embedding the images in a three-dimensional space).

The image processor 230 analyzes the observation image as a moving image to detect the amount of misregistration between an image of each frame and a predetermined image. The image processor 230 outputs the misregistration amount thus detected to the controller 210 (the main controller 211) for controlling tracking. The predetermined image is an image determined prior to the start of the process of detecting the misregistration amount. As an example of the predetermined image may be cited an image of the first frame of the observation image after the start of tracking. Hereinafter, the predetermined image is referred to as "base image", and the image of each frame is referred to as "target image". The misregistration amount refers to a rotational movement amount of a sub-pixel level (less than 1 pixel) in a rotation direction (z axis direction) between the base image and the target image, and a parallel movement amount of a sub-pixel level in the xy plane between the base image and the target image. In the present embodiment, the misregistration amount is detected by a calculation in arithmetic processing to be described below. Incidentally, the base image corresponds to an example of "first image", and the target image corresponds to an example of "second image".

The image processor 230 first calculates a rotational movement amount between the base image and the target image at the sub-pixel level, and performs registration between the base image and the target image in the rotation direction based on the rotational movement amount. The image processor 230 then calculates a parallel movement amount between the base image and the target image, which have been registered to each other, at the sub-pixel level.

To realize such processing, the image processor 230 includes a rotational movement amount calculator 231, a registration unit 232, and a parallel movement amount calculator 233. Incidentally, similarly to general digital cameras, the image processor 230 or the fundus camera unit 2 converts an image signal from the CCD image sensors 35 and 38 into a digital signal. The digital signal may be temporarily stored in a memory (not illustrated), for example. The digital signal stored in the memory is subjected to the process of the rotational movement amount calculator 231 and thereafter as a signal corresponding to each of the base image and the target image.

The image processor 230 performs a phase only correlation process (described later) to calculate the rotational movement amount and the parallel movement amount between the base image and the target image. In this case, the image processor 230 calculates phase only correlation (POC) data (first data) in advance for the base image to be used in the phase only correlation process. Hereinafter, the POC data for the base image may sometimes be referred to as "base POC data", and the POC data for the target image may sometimes be referred to as "target POC data". When the target image POC data (second data) is calculated, the image processor 230 continues the phase only correlation process based on the target POC data and the base POC data obtained in advance. This aims to reduce the processing load and the processing time to calculate a slight misregistration amount.

(Phase Only Correlation Process)

The phase only correlation process of the present embodiment uses, for example, a known phase only correlation function. In the present embodiment, the phase only correlation function as disclosed in Non-Patent Document 1 is used.

First, it is assumed that the base image and the target image having an image size of $N_1 \times N_2$ ($N_1$ and $N_2$ are positive integers) are represented by $f(n_1, n_2)$ and $g(n_1, n_2)$, respectively. It is also assumed herein that, in the discrete space, $n_1=-M_1, \ldots, M_1$, $N_1=2M_1+1$ ($M_1$ is a positive integer), and the result of two-dimensional discrete Fourier transform (DFT) of $f(n_1, n_2)$ is $F(k_1, k_2)$. Then, $F(k_1, k_2)$ is represented by Equation (1) as follows:

[Equation 1]

$$F(k_1, k_2) = \sum_{n_1=-M_1}^{M_1} \sum_{n_2=-M_2}^{M_2} f(n_1, n_2) W_{N_1}^{k_1 n_1} W_{N_2}^{k_2 n_2} = A_F(k_1, k_2) e^{j\theta_F(k_1, k_2)} \quad (1)$$

$(k_1 = -M_1, \ldots, M_1, k_2 = -M_2, \ldots, M_2, W_{N_1} = e^{-j\frac{2\pi}{N_1}}, W_{N_2} = e^{-j\frac{2\pi}{N_2}})$ In Equation (1), $A_F(k_1, k_2)$ is the amplitude component of $f(n_1, n_2)$, and $e^{j\theta_F(k_1, k_2)}$ is the phase component of $f(n_1, n_2)$.

Similarly, it is assumed that, in the discrete space, $n_2 = -M_2, \ldots, M_2$, $N_2 = 2M_2 + 1$ ($M_2$ is a positive integer), and the result of two-dimensional DFT of $g(n_1, n_2)$ is $G(k_1, k_2)$. Then, $G(k_1, k_2)$ is represented by Equation (2) as follows:

[Equation 2]

$$G(k_1, k_2) = \sum_{n_1=-M_1}^{M_1} \sum_{n_2=-M_2}^{M_2} g(n_1, n_2) W_{N_1}^{k_1 n_1} W_{N_2}^{k_2 n_2} = A_G(k_1, k_2) e^{j\theta_G(k_1, k_2)} \quad (2)$$

$(k_1 = -M_1, \ldots, M_1, k_2 = -M_2, \ldots,$ $M_2, W_{N_1} = e^{-j\frac{2\pi}{N_1}}, W_{N_2} = e^{-j\frac{2\pi}{N_2}})$ In Equation (2), $A_G(k_1, k_2)$ is the amplitude component of $g(n_1, n_2)$, and $e^{j\theta_G(k_1, k_2)}$ is the phase component of $g(n_1, n_2)$.

Using Equations (1) and (2), the phase only synthesis function used in the phase only synthesis process is defined by Equation (3) as follows:

[Equation 3]

$$\hat{R}(k_1, k_2) = \frac{F(k_1, k_2)\overline{G(k_1, k_2)}}{|F(k_1, k_2)\overline{G(k_1, k_2)}|} = e^{j\theta(k_1, k_2)} \quad (3)$$

where $\overline{G(k_1, k_2)}$ is the complex conjugate of $G(k_1, k_2)$, and $\theta(k_1, k_2) = \theta_F(k_1, k_2) - \theta_G(k_1, k_2)$ By applying a two-dimensional inverse discrete Fourier transform (IDFT) to the phase only synthesis function represented by Equation (3), the phase only correlation function of the present embodiment is represented by Equation (4) as follows:

[Equation 4]

$$\hat{r}(n_1, n_2) = \frac{1}{N_1 N_2} \sum_{k_1=-M_1}^{M_1} \sum_{k_2=-M_2}^{M_2} \hat{R}(k_1, k_2) W_{N_1}^{-k_1 n_1} W_{N_2}^{-k_2 n_2} \quad (4)$$

An image obtained by shifting a two-dimensional image $s_c(x_1, x_2)$ defined in a continuous space by a minute movement amount $\delta_1$ in the $x_1$ direction and by a minute movement amount $\delta_2$ in the $x_2$ direction is represented as $sc(x_1 - \delta_1, x_2 - \delta_2)$. The two-dimensional image $f(n_1, n_2)$ sampled at a sampling interval $T_1$ in the discrete space is defined by Equation (5) as follows:

[Equation 5]

$$f(n_1, n_2) = s_c(x_1, x_2)|_{x_1 = n_1 T_1, x_2 = n_2 T_2} \quad (5)$$

Similarly, the two-dimensional image $g(n_1, n_2)$ sampled at a sampling interval $T_2$ in the discrete space is defined by Equation (6) as follows:

[Equation 6]

$$g(n_1, n_2) = s_c(x_1 - \delta_1, x_2 - \delta_2)|_{x_1 = n_1 T_1, x_2 = n_2 T_2} \quad (6)$$

In Equations (5) and (6), and $n_1 = -M_1, \ldots, M_1$, $n_2 = -M_2, \ldots, M_2$. Thus, the phase only correlation function related to the two-dimensional images $f(n_1, n_2)$ and $g(n_1, n_2)$ in the discrete space is represented in general form as Equation (7) as follows:

[Equation 7]

$$\hat{r}(n_1, n_2) \approx \frac{\alpha}{N_1 N_2} \frac{\sin\{\pi(n_1 + \delta_1)\}}{\sin\{\frac{\pi}{N_1}(n_1 + \delta_1)\}} \frac{\sin\{\pi(n_2 + \delta_2)\}}{\sin\{\frac{\pi}{N_2}(n_2 + \delta_2)\}} \quad (7)$$

where $\alpha = 1$.

Figure 4:
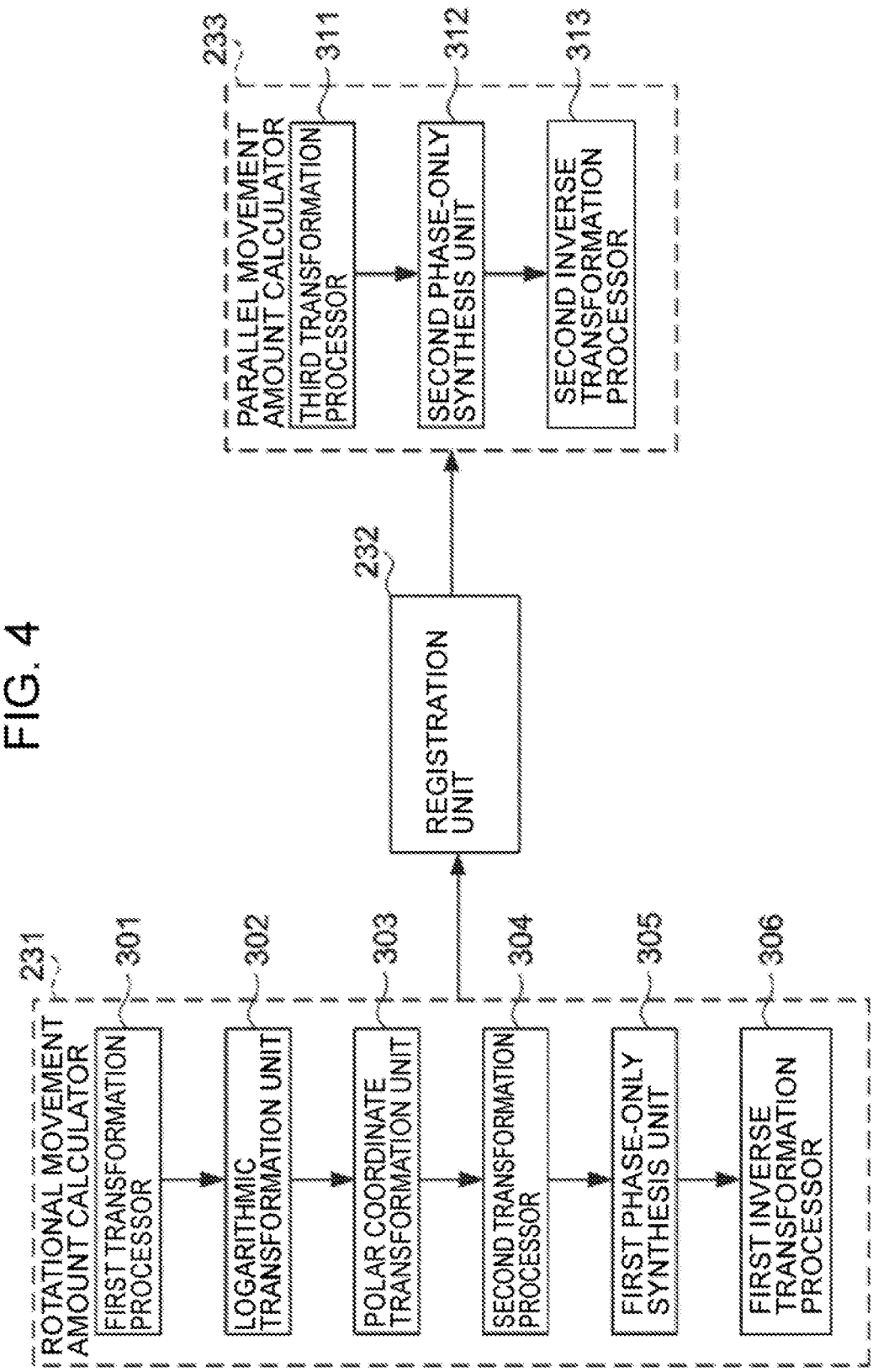
FIG. 4 is a schematic block diagram illustrating an example of the configuration of the ophthalmologic apparatus of the embodiment.

With reference to FIG. 4, a description is given of an example of the configuration of the image processor 230 that performs the phase only correlation process as mentioned above.

(Rotational Movement Amount Calculator)

The rotational movement amount calculator 231 calculates a rotational movement amount between the base image and the target image. Specifically, the rotational movement amount calculator 231 performs a phase only correlation process on the base image and the target image to obtain the rotational movement amount therebetween. The rotational movement amount calculator 231 includes a first transformation processor 301, a logarithmic transformation unit 302, a polar coordinate transformation unit 303, a second transformation processor 304, a first phase only synthesis unit 305, and a first inverse transformation processor 306.

The first transformation processor 301 performs a two-dimensional DFT process on the base image. The first transformation processor 301 performs the two-dimensional DFT process also on the target image. The two-dimensional DFT process performed by the first transformation processor 301 includes two-dimensional DFT, and a known shift process for shifting the quadrant with respect to the result of the two-dimensional DFT. Hereinafter, this shift process may be referred to as "shift". Note that the two-dimensional DFT performed by the first transformation processor 301 may be two-dimensional FFT.

The logarithmic transformation unit 302 applies a logarithmic transformation to the calculation result for the base image obtained by the first transformation processor 301. Further, the logarithmic transformation unit 302 applies a logarithmic transformation also to the calculation result for the target image obtained by the first transformation processor 301. The logarithmic transformation performed by the logarithmic transformation unit 302 has the effect of compressing the amplitude spectrum that has a tendency to concentrate in the low-frequency region of the spatial frequency in a natural image.

The polar coordinate transformation unit 303 applies a polar coordinate transformation to the calculation result for the base image obtained by the logarithmic transformation unit 302. Further, the polar coordinate transformation unit 303 applies a polar coordinate transformation also to the calculation result for the target image obtained by the logarithmic transformation unit 302. When the logarithmic transformation is not performed by the logarithmic transformation unit 302, the polar coordinate transformation unit 303 applies a polar coordinate transformation to the calculation results for the base image and the target image obtained by the first transformation processor 301. The polar coordinate transformation performed by the polar coordinate transformation unit 303 is the process of converting the movement amount in the rotation direction into the movement amount in the parallel direction ($n_1$ direction, $n_2$ direction) in Equations (1) to (7).

As illustrated in Equation (1), the second transformation processor 304 performs the two-dimensional DFT process (two-dimensional DFT+shift) on the calculation result for the base image obtained by the polar coordinate transformation unit 303. Prior to the arithmetic processing of the first phase only synthesis unit 305, the processing result of the base image obtained by the second transformation processor 304 is stored in, for example, the storage 212 in advance as the base POC data (first data) normalized by the amplitude component. As illustrated in Equation (2), the second transformation processor 304 performs the two-dimensional DFT process (two-dimensional DFT+shift) on the calculation result for the target image obtained by the polar coordinate transformation unit 303. Incidentally, the two-dimensional DFT performed by the second transformation processor 304 may also be two-dimensional FFT.

As illustrated in Equation (3), the first phase only synthesis unit 305 performs a phase only synthesis process for synthesizing the base POC data (first data) previously obtained for the base image and the target POC data (second data) normalized by the amplitude component based on the calculation result for the target image obtained by the second transformation processor 304.

The first inverse transformation processor 306 performs a two-dimensional IDFT process on the calculation result obtained by the first phase only synthesis unit 305. The two-dimensional IDFT process performed by the first inverse transformation processor 306 includes two-dimensional IDFT, and a known shift process for shifting the quadrant with respect to the result of the two-dimensional IDFT. Note that the two-dimensional IDFT may be a two-dimensional inverse fast Fourier transform (IFFT).

The rotational movement amount calculator 231 calculates a rotational movement amount based on the calculation result obtained by the first inverse transformation processor 306. Specifically, the rotational movement amount calculator 231 specifies the peak position based on the calculation result obtained by the first inverse transformation processor 306 to thereby calculate the movement amount (rotational movement amount, misregistration amount) in the rotation direction at the pixel level. Thereafter, the rotational movement amount calculator 231 specifies the pixel location at which the correlation value of the phase only correlation function represented by Equation (7) becomes the maximum in the vicinity of the peak position specified at the pixel level, thereby obtaining the movement amount (rotational movement amount, misregistration amount) in the rotation direction at the sub-pixel level. The rotational movement amount calculator 231 corresponds to an example of "rotational movement amount calculator".

The rotational movement amount calculator 231 has been described as calculating the movement amount of the target image in the rotation direction by using the base image as a reference; however, it is not so limited. The rotational movement amount calculator 231 may calculate the movement amount of the base image in the rotation direction by using the target image as a reference.

The rotational movement amount calculator 231 need not necessarily calculate the rotational movement amount through the phase only correlation process. The rotational movement amount calculator 231 may calculate the rotational movement amount by a known technique, and output the rotational movement amount thus obtained to the registration unit 232.

(Registration Unit)

The registration unit 232 performs registration in the rotation direction between the base image and the target image based on the rotational movement amount calculated by the rotational movement amount calculator 231. Specifically, the registration unit 232 registers the target image with respect to the base image, which is used as a reference, in the rotation direction based on the rotational movement amount calculated by the rotational movement amount calculator 231 such that the rotational movement amount becomes zero. Incidentally, the registration unit 232 may register the base image with respect to the target image, which is used as a reference, in the rotation direction based on the rotational movement amount calculated by the rotational movement amount calculator 231. The registration unit 232 corresponds to an example of "registration part".

(Parallel Movement Amount Calculator)

The parallel movement amount calculator 233 calculates a parallel movement amount between the base image and the target image registered by the registration unit 232. Specifically, the parallel movement amount calculator 233 applies phase only correlation to the base image and the target image registered by the registration unit 232 to obtain the parallel movement amount therebetween. The parallel movement amount calculator 233 includes a third transformation processor 311, a second phase only synthesis unit 312, and a second inverse transformation processor 313.

As illustrated in Equation (1), the third transformation processor 311 performs the two-dimensional DFT process (two-dimensional DFT+shift) on the base image. Prior to the arithmetic processing of the second phase only synthesis unit 312, the processing results of the base image obtained by the third transformation processor 311 is stored in, for example, the storage 212 in advance as the base POC data (third data) normalized by amplitude component. As illustrated in Equation (2), the third transformation processor 311 performs the two-dimensional DFT process (two-dimensional DFT+shift) on the target image. Incidentally, the two-dimensional DFT performed by the third transformation processor 311 may also be two-dimensional FFT.

As illustrated in Equation (3), the second phase only synthesis unit 312 performs a phase only synthesis process for synthesizing the base POC data (third data) previously obtained for the base image and the target POC data (fourth data) normalized by amplitude component based on the calculation result for the target image obtained by the third transformation processor 311.

The second reverse transformation processor 313 performs a two-dimensional IDFT process (two-dimensional IDFT+shift) on the calculation result obtained by the second phase only synthesis unit 312. The two-dimensional IDFT performed by the second inverse transformation processor 313 may be two-dimensional IFFT.

The parallel movement amount calculator 233 calculates a parallel movement amount based on the calculation result obtained by the second inverse transformation processor 313. Specifically, the parallel movement amount calculator 233 specifies the peak position based on the calculation result obtained by the second inverse transformation processor 313 to thereby obtain the movement amount (parallel movement amount, misregistration amount) in the parallel direction at the pixel level. Thereafter, the parallel movement amount calculator 233 specifies the pixel location at which the correlation value of the phase only correlation function represented by Equation (7) becomes the maximum in the vicinity of the peak position specified at the pixel level, thereby obtaining the movement amount (parallel movement amount, misregistration amount) in the parallel direction at the sub-pixel level. The parallel movement amount calculator 233 corresponds to an example of "parallel movement amount calculator".

The parallel movement amount calculator 233 has been described as calculating the movement amount of the target image in the parallel direction based on the base image; however, it is not so limited. The parallel movement amount calculator 233 may calculate the movement amount of the base image in the parallel direction based on the target image.

Of the rotational movement amount and the parallel movement amount calculated by the image processor 230, at least the parallel movement amount is output to the controller 210. The controller 210 (the main controller 211) controls an optical system driver 90 based on the parallel movement amount obtained by the image processor 230 to move the optical system provided in the fundus camera unit 2 three-dimensionally, thereby performing tracking. The controller 210 (the main controller 211) may control the optical system driver 90 based on the rotational movement amount calculated by the image processor 230 to move (rotate) the optical system provided in the fundus camera unit 2 three-dimensionally, thereby performing tracking.

The image processor 230 that functions as above includes, for example, a microprocessor, RAM, ROM, a hard disk drive, a circuit board, and the like. The storage device such as a hard disk drive stores, in advance, computer programs for causing the microprocessor to implement the above functions.

(User Interface)

A user interface 240 includes the display 240A and an operation unit 240B. The display 240A includes the aforementioned display device of the arithmetic and control unit 200 and a display 3. The operation unit 240B includes the aforementioned operation device of the arithmetic and control unit 200. The operation unit 240B may include various types of buttons and keys provided on the case of the ophthalmologic apparatus 1 or the outside. For example, if the fundus camera unit 2 has a case similar to those of conventional fundus cameras, the operation unit 240B may include a joy stick, an operation panel, and the like provided to the case. Besides, the display 240A may include various types of display devices, such as a touch panel, arranged on the case of the fundus camera unit 2.

Note that the display 240A and the operation unit 240B need not necessarily be formed as separate devices. For example, a device like a touch panel, which has a display function integrated with an operation function, can be used. In such cases, the operation unit 240B includes the touch panel and a computer program. The content of operation on the operation unit 240B is fed to the controller 210 as an electric signal. Moreover, operations and inputs of information may be performed by using a graphical user interface (GUI) displayed on the display 240A and the operation unit 240B.

[Regarding Scanning of Signal Light and OCT Image]

Described below are the scanning of the signal light LS and an OCT image.

Examples of scan modes of the ophthalmologic apparatus 1 for scanning the signal light LS include horizontal scan, vertical scan, cross scan, radial scan, circle scan, concentric scan, helical (spiral) scan, and the like. The scan modes are selectively used as appropriate in consideration of the site of the fundus to be observed, an object to be analyzed (retinal thickness, etc.), time required for scanning, scanning accuracy, and the like.

In the horizontal scan mode, the signal light LS is scanned in the horizontal direction (x direction). The horizontal scan mode includes the scan of the signal light LS along a plurality of scan lines arranged in the vertical direction (y direction) and extending in the horizontal direction. In this mode, the interval between the scan lines can be arbitrarily set. Besides, the scan lines are adjacent to one another at sufficiently narrow intervals to form a three-dimensional image as described above (3D scan). The same applies to the vertical scan.

In the cross scan mode, the signal light LS is scanned along a cruciform trajectory consisting of two straight trajectories that are perpendicular to each other. In the radial scan mode, the signal light LS is scanned along radial trajectories including a plurality of straight trajectories arranged at a predetermined angle. The cross scan is an example of the radial scan.

In the circle scan mode, the signal light LS is scanned along a circular trajectory. In the concentric scan mode, the signal light LS is scanned along a plurality of circular trajectories arranged concentrically around a predetermined center position. The circle scan is an example of the concentric scan. In the helical scan mode, the signal light LS is scanned along a helical (spiral) trajectory while the rotation radius is gradually reduced (or increased).

The galvano-scanner 42 is configured to scan the signal light LS in directions perpendicular to each other, and therefore, is capable of scanning the signal light LS in the x and y directions independently. Further, by controlling the orientations of two galvanometer mirrors in the galvano-scanner 42 at the same time, the signal light LS can be scanned along an arbitrary trajectory on the xy plane. Thus, it is possible to implement a variety of scan modes as described above.

By scanning the signal light LS in the manner described above, it is possible to acquire a tomographic image in a plane spanned in a direction along the scan lines (scan trajectories) and the depth direction of the fundus (z direction). Besides, particularly when the scan lines are arranged at a narrow interval, the three-dimensional image as described above can be obtained.

An area on the fundus Ef to be scanned by the signal light LS as described above, i.e., an area on the fundus Ef subjected to OCT measurement, is referred to as "scan area". The scan area in a three-dimensional scan is a rectangular area, in which a plurality of horizontal scan lines is arranged. The scan area of a concentric scan is a disc-shaped area surrounded by the trajectory of circle scanning with the largest diameter. In addition, the scan area in a radial scan is a disc-shaped (or polygonal) area connecting the ends of the scan lines.

[Operation]

Described below is the operation of the ophthalmologic apparatus 1.

Figure 5:
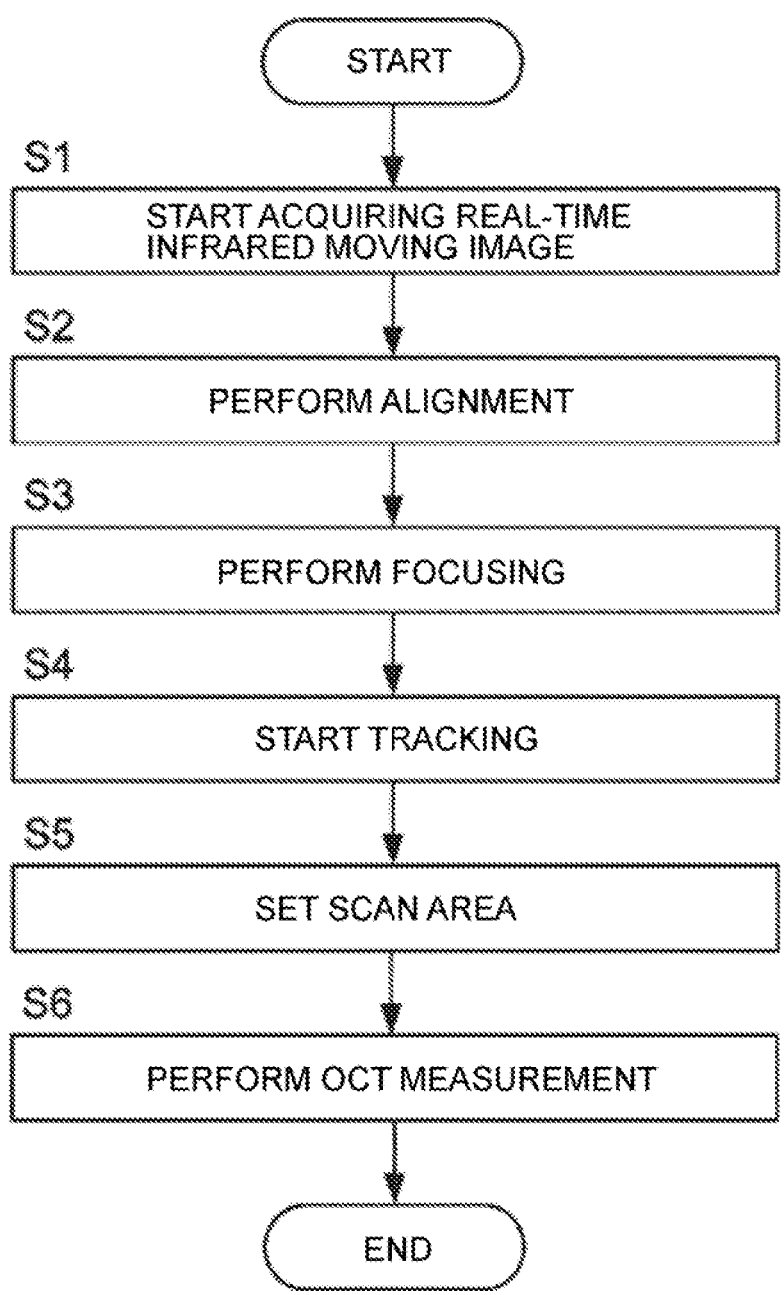
FIG. 5 is a flowchart illustrating an example of the operation of the ophthalmologic apparatus of the embodiment.

FIG. 5 illustrates an example of the operation of the ophthalmologic apparatus 1. In the present operation example, a case is described in which OCT measurement is performed after the correction of a misregistration amount calculated by the image processor 230. The present operation example includes position alignment between the subject's eye E and the optical system of the apparatus based on an image and setting of a scan area based on an image. The position alignment includes alignment (automatic alignment), focusing (automatic focusing), and tracking (automatic tracking) for OCT measurement.

(S1: Start Acquiring Real-Time Infrared Moving Image)

First, the fundus Ef is continuously irradiated with the illumination light (which has become near-infrared light via the visible cut filter 14) output from the observation light source 11, thereby starting the acquisition of a near-infrared moving image of the fundus Ef. The near-infrared moving image is acquired in real time until the end of the continuous irradiation. The frames of the moving image are temporarily stored in a frame memory (the storage 212) and sequentially sent to the image processor 230.

Incidentally, an alignment indicator and a split target are projected onto the subject's eye E respectively by the alignment optical system 50 and the focus optical system 60. Accordingly, the alignment indicator and the split target are illustrated in the near-infrared moving image. Alignment and focusing can be performed using them. Further, a fixation target generated by the LCD 39 is also projected onto the subject's eye E. The subject is instructed to fixate the eye on the fixation target.

(S2: Perform Alignment)

The image processor 230 sequentially analyzes frames acquired by capturing a moving image of the subject's eye E with the optical system to obtain the position of the alignment indicator, thereby calculating the movement amount of the optical system. The controller 210 controls the optical system driver 90 based on the movement amount of the optical system obtained by the image processor 230 to perform automatic alignment.

(S3: Perform Focusing)

The image processor 230 sequentially analyzes frames acquired by capturing a moving image of the subject's eye E with the optical system to obtain the position of the split target, thereby calculating the movement amount of the focusing lens 31. The controller 210 controls the focusing driver 31A based on the movement amount of the focusing lens 31 obtained by the image processor 230 to perform automatic focusing.

(S4: Start Tracking)

Subsequently, the controller 210 starts automatic tracking. Specifically, the image processor 230 analyzes frames sequentially acquired by capturing a moving image of the subject's eye E with the optical system in real time, and monitors the movement (positional change) of the subject's eye E. The controller 210 controls the optical system driver 90 to move the optical system in accordance with the position of the subject's eye E sequentially obtained. Thereby, the optical system can follow the movement of the subject's eye E in real time. Thus, it is possible to maintain a good positional relationship with proper alignment and focus. The image processor 230 sequentially calculates a misregistration amount at the sub-pixel level between the base image and the target image. The controller 210 moves the optical system to correct the misregistration amount calculated by the image processor 230 for each frame or every the predetermined number of frames.

(S5: Set Scan Area)

The controller 210 displays the near-infrared moving image on the display 240A in real time. The user sets a scan area on the near-infrared moving image using the operation unit 240B. The scan area may be a one-dimensional region or a two-dimensional region.

For example, if the scan mode of the signal light LS, a site of interest (optic papilla, macula, lesion, etc.) or the like is set in advance, the controller 210 may set the scan area based on the content of the setting. Specifically, the image processor 230 can perform image analysis to specify the site of interest, and then the controller 210 can set an area in a predetermined pattern to include the site of interest (e.g., such that the site of interest is located in the center of the area).

To set the same scan area as in OCT measurement taken in the past (so-called follow-up), the controller 210 can reproduce and set the past scan area on the real-time near-infrared moving image. As a specific example, the controller 210 stores information (scan mode, etc.) representing the scan area set in the past examination and a near-infrared fundus image (a still image, may be, for example, a frame) in the storage 212 in association with each other (in practice, they are associated also with patient ID and left/right eye information). The controller 210 performs registration between the past near-infrared fundus image and a frame of the real-time near-infrared moving image, and specifies an image area in the real-time image corresponding to the scan area in the past image. Thereby, the scan area used in the past examination is set in the real-time near-infrared moving image.

(S6: Perform OCT Measurement)

The controller 210 controls a light source unit 120 and the optical path length changing unit 41 as well as controlling the galvano-scanner 42 based on the scan area set in step S5 to perform OCT measurement of the fundus Ef. The image forming unit 220 forms a tomographic image of the fundus Ef based on a detection signal obtained. When three-dimensional scan is set as the scan mode, the image processor 230 forms a three-dimensional image of the fundus Ef based on a plurality of tomographic images formed by the image forming unit 220. Then, the operation example is completed (END).

Note that steps S4 and S5 described above may be performed in reverse order. Besides, in steps S4 and S5 described above, the near-infrared moving image is displayed, and then a scan area is set thereon. However, the scan area need not necessarily be set in this way. For example, while one frame image (referred to as "reference image") of the near-infrared moving image is being displayed, automatic tracking is performed in the background. When a scan area is set on the reference image, the controller 210 performs registration between the reference image and the image being subjected to the automatic tracking to specify an image area in the real-time near-infrared moving image corresponding to the scan area set on the reference image. Through this process, the scan area can also be set in the real-time near-infrared moving image as in steps S4 and S5 described above. Further, with this process, the scan area can be set on a still image. This facilitates the setting and increases the accuracy thereof compared to the case of setting the scan area on a moving image being subjected to automatic tracking at the present time.

In the present operational example, the optical system driver 90 corresponds to an example of "driver", and the controller 210 corresponds to an example of "controller", which controls the optical system driver 90.

[Effects]

The ophthalmologic apparatus 1 is an example of the ophthalmologic apparatus according to the present embodiment. Described below are the effects of the ophthalmologic apparatus of the present embodiment.

According to the present embodiment, an ophthalmologic apparatus includes an optical system (e.g., the fundus camera unit 2), a rotational movement amount calculator (e.g., the rotational movement amount calculator 231), a registration unit (e.g., the registration unit 232), a parallel movement amount calculator (e.g., the parallel movement amount calculator 233), a driver (e.g., the optical system driver 90), and a controller (e.g., the controller 210 and the main controller 211).

The optical system is used to capture a moving image of the subject's eye. The rotational movement amount calculator is configured to calculate a rotational movement amount between a first image and a second image included in the moving image acquired by the optical system. The registration unit is configured to perform registration between the first image and the second image in the rotation direction based on the rotational movement amount calculated by the rotational movement amount calculator. The parallel movement amount calculator is configured to perform a phase only correlation process on the first image and the second image registered by the registration unit to calculate a parallel movement amount between the first image and the second image. The driver is configured to move the optical system. The controller is configured to control the driver based on the parallel movement amount calculated by the parallel movement amount calculator.

The rotational movement amount is the amount of movement in the rotation direction. Here, the rotation direction is a direction about the axis that intersects the first image and the second image. In the embodiment, the rotation direction is a direction about the optical axis of the optical system configured to capture the first image and the second image. The parallel movement amount is the amount of movement in the parallel direction. Here, the parallel direction may be any direction on a plane parallel to the first image and the second image.

The ophthalmologic apparatus thus configured can calculate a rotational movement amount between the first image and the second image of the moving image captured at different times by the optical system, and perform registration between the first image and the second image based on the rotational movement amount calculated. Thereafter, a phase only correlation process can be performed on the first image and the second image registered to each other. Thereby, the parallel movement amount between the first image and the second image can be calculated at the sub-pixel level, and the optical system can be moved based on the parallel movement amount calculated. Thus, even a slight misregistration can be detected with high accuracy. Further, high precision tracking can be achieved by moving the optical system based on the amount of the slight misregistration detected.

The ophthalmologic apparatus of the embodiment may also calculate the rotational movement amount at the sub-pixel level by performing the phase only correlation process. In this case, the rotational movement amount calculator performs the phase only correlation process on the first image and the second image to calculate the rotational movement amount between the first image and the second image.

With the ophthalmologic apparatus thus configured, registration can be performed between the first image and the second image based on the rotational movement amount calculated at the sub-pixel level. This makes it possible to detect a finer misregistration, thereby achieving higher precision tracking.

In the ophthalmologic apparatus of the embodiment, the rotational movement amount calculator may include a first transformation processor (e.g., the first transformation processor 301), a polar coordinate transformation unit (e.g., the polar coordinate transformation unit 303), a second transformation processor (e.g., the second transformation processor 304), a first phase only synthesis unit (e.g., the first phase only synthesis unit 305), and a first inverse transformation processor (e.g., the first inverse transformation processor 306). In this case, the first transformation processor is configured to apply DFT to the second image. The polar coordinate transformation unit is configured to apply a polar coordinate transformation to a calculation result for the second image obtained by the first transformation processor. The second transformation processor is configured to apply DFT to a calculation result for the second image obtained by the polar coordinate transformation unit. The first phase only synthesis unit is configured to perform a phase only synthesis process for synthesizing first data obtained for the first image in advance and second data based on a calculation result obtained for the second image by the second transformation processor. The first inverse transformation processor is configured to apply IDFT to a calculation result obtained by the first phase only synthesis unit. The rotational movement amount calculator is configured to calculate the rotational movement amount based on a calculation result obtained by the first inverse transformation processor. The phase only synthesis process of the embodiment includes various transformations described above.

With this configuration, the phase only synthesis process is performed to synthesize the first data obtained in advance and the second data obtained by a known transformation process to thereby obtain the rotational movement amount. This contributes to the realization of high-precision tracking as well as achieving a reduction in processing loads and processing time.

In the ophthalmologic apparatus of the embodiment, the rotational movement amount calculator may apply the same transformation as applied to the second image to the first image to generate the first data. In this case, the first transformation processor is configured to apply DFT to the first image. The polar coordinate transformation unit is configured to apply the polar coordinate transformation to a calculation result for the first image obtained by the first transformation processor. The second transformation processor is configured to apply DFT to a calculation result for the first image obtained by the polar coordinate transformation unit to generate the first data.

With this configuration, the ophthalmologic apparatus generates the first data of the first image to be subjected to the phase only synthesis process as in the case of the second image. Accordingly, a rotational movement amount can be calculated with high accuracy for a desired moving image, and thus can be applied to tracking.

In the ophthalmologic apparatus of the embodiment, the parallel movement amount calculator may include a third transformation processor (e.g., the third transformation processor 311), a second phase only synthesis unit (e.g., the second phase only synthesis unit 312), and a second inverse transformation processor (e.g., the second inverse transformation processor 313). The third transformation processor is configured to apply DFT to the second image registered by the registration unit. The second phase only synthesis unit is configured to perform the phase only synthesis process for synthesizing third data obtained for the first image in advance and fourth data based on a calculation result obtained for the second image by the third transformation processor. The second inverse transformation processor is configured to apply IDFT to a calculation result obtained by the second phase only synthesis unit. The parallel movement amount calculator is configured to calculate the parallel movement amount based on a calculation result obtained by the second inverse transformation processor.

With this configuration, the phase only synthesis process is performed to synthesize the third data obtained in advance and the fourth data obtained by a known transformation process to thereby obtain the parallel movement amount. This contributes to the realization of high-precision tracking as well as achieving a reduction in processing loads and processing time.

In the ophthalmologic apparatus of the embodiment, the parallel movement amount calculator may apply the same transformation as applied to the second image to the first image registered by the registration unit to generate the third data. In this case, the third transformation processor is configured to apply DFT to the first image that has been registered by the registration unit to generate the third data.

With this configuration, the ophthalmologic apparatus generates the third data for the first image to be subjected to the phase only synthesis process as in the case of the second image. Accordingly, a parallel movement amount can be calculated with accuracy for a desired moving image, and thus can be applied to tracking.

Second Embodiment

In the present embodiment, a description is given of an ophthalmologic apparatus configured to perform parallel processing to implement the high-speed calculation of the misregistration amount at the sub-pixel level.

[Configuration]

The ophthalmologic apparatus of the present embodiment is of basically the same configuration as that of the first embodiment except the controller 210 and the image processor 230 (see FIGS. 1 and 2). In the present embodiment, the functions of the controller 210 and the image processor 230 are implemented by, for example, the arithmetic processor 400.

Figure 6:
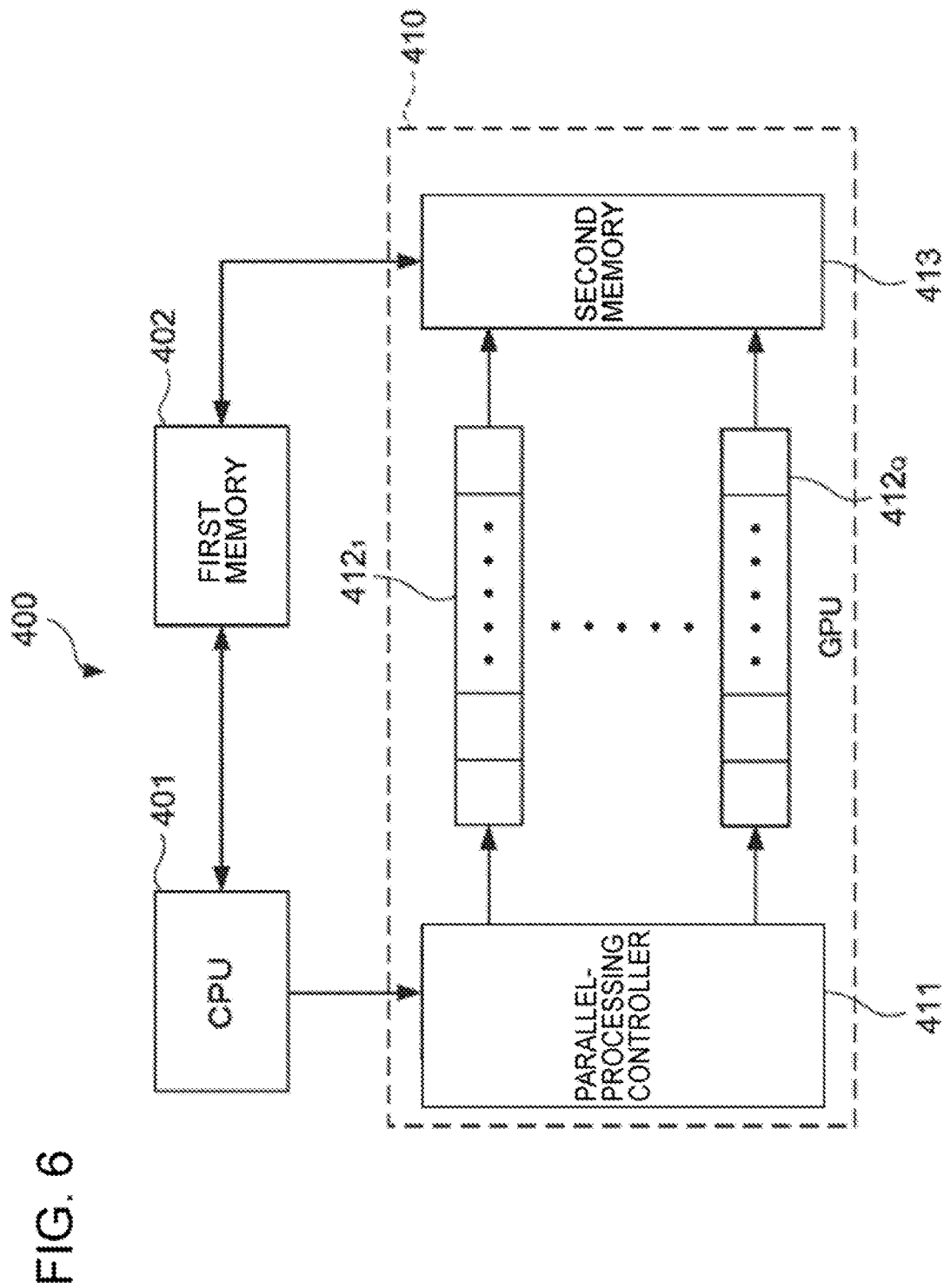
FIG. 6 is a schematic block diagram illustrating an example of the configuration of an ophthalmologic apparatus according to another embodiment.

With reference to FIG. 6, the configuration of the arithmetic processor 400 is described.

(Arithmetic Processor)

The arithmetic processor 400 includes a central processing unit (CPU) 401, a first memory 402, and a graphical processing unit (GPU) 410.

The CPU 401 reads a program stored in the first memory 402, and executes it to perform processing corresponding to the program, thereby, for example, implementing the functions of the controller 210 (the main controller 211). Further, the CPU 401 runs the kernel function to control the GPU 410. The first memory 402 implements the functions of the storage 212. The first memory 402 is used as a storage area for programs executed by the CPU 401 and processing results, or a work area.

The GPU 410 includes a parallel-processing controller 411, a plurality of arithmetic processors $412_1$ to $412_Q$ includes a (Q is a natural number equal to or larger than 2), and a second memory 413. The parallel-processing controller 411 is configured to control the parallel processing of operations performed by the arithmetic processors $412_1$ to $412_Q$. The CPU 401 specifies the content of the operations and the mode of parallel processing. As a parallel processing mode, for example, the CPU 401 specifies the number of threads and the number of blocks. The arithmetic processors $412_1$ to $412_Q$ each include an instruction unit, a plurality of operation units, and a register. The arithmetic processors $412_1$ to $412_Q$ are configured to be able to simultaneously execute the same processing specified by the CPU 401 in parallel. The parallel-processing controller 411 controls the arithmetic processors $412_1$ to $412_Q$ to perform processing specified by the CPU 401 in parallel. Specifically, the parallel-processing controller 411 repeatedly uses the arithmetic processors $412_1$ to $412_Q$ to perform processing of threads more than Q. The second memory 413 functions as a shared memory shared by the arithmetic processors $412_1$ to $412_Q$. The second memory 413 is used as a storage area for processing results obtained by the arithmetic processors, or a work area.

The GPU 410 performs the arithmetic processing of the rotational movement amount calculator 231 and the parallel movement amount calculator 233 of the image processor 230. The CPU 401 performs processing other than the arithmetic processing performed by the GPU 410.

The CPU 401 performs the processing according to programs stored in the first memory 402, and thereby transfers data from the first memory 402 to the GPU 410 as well as running the kernel function to be executed in the GPU 410. Then, the GPU 410 performs a process specified by the CPU 401 on data in the second memory 413 prepared by the CPU 401. The processing result obtained by the GPU 410 is stored in the second memory 413. The CPU 401 controls data transfer to return the processing result obtained by the GPU 410 from the second memory 413 to the first memory 402. Thus, it is possible to acquire the processing result obtained at a high speed by the GPU 410.

[Operation]

Described below is the operation of the ophthalmologic apparatus of the present embodiment. The ophthalmologic apparatus of the present embodiment operates basically in the same manner as that of the first embodiment except for the details of the calculation of the rotational movement amount and the parallel movement amount. The following specifically describes the calculation of the rotational movement amount and the parallel movement amount using the arithmetic processor 400 of the present embodiment.

Figure 7:
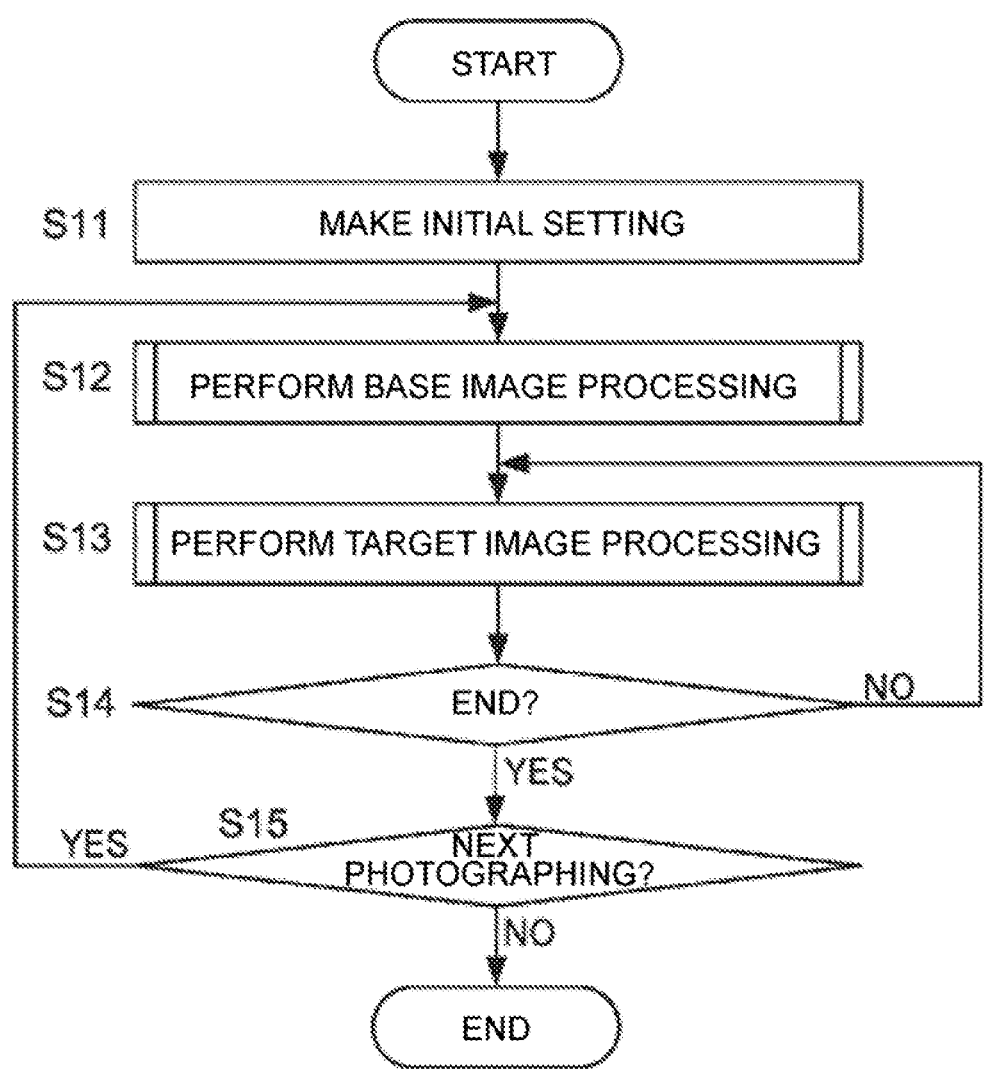
FIG. 7 is a flowchart illustrating an example of the operation of the ophthalmologic apparatus of the embodiment.

FIG. 7 illustrates a specific example of the process of calculating the rotational movement amount and the parallel movement amount in the ophthalmologic apparatus of the embodiment. In the present operation example, the process is triggered by the start of tracking instructed by the user.

(S11: Make Initial Setting)

First, the CPU 401 sets a library and a constant for controlling the GPU 410, secures a storage area for performing the process, secures the first memory 402 and the second memory 413, and sets threads (e.g., 32×32×1) or blocks (e.g., 11×11×1) for the GPU 410. The arithmetic processors $412_1$ to $412_Q$ each process one of the threads. The CPU 401 instructs the GPU 410 so that each of the threads performs processing for one pixel (e.g., calculation of each of Equations (1) to (7)).

(S12: Perform Base Image Processing)

When the user instructs the start of tracking, the CPU 401 performs base image processing to perform a phase only correlation process on a base image. The base image is transferred from the first memory 402 to the second memory 413 under the control of the CPU 401. Along with this, the CPU 401 specifies the content of a process to be performed by the GPU 410 in the phase only correlation process for the base image, and instructs the GPU 410 to perform the process. The base image processing is described in detail later.

(S13: Perform Target Image Processing)

The CPU 401 performs target image processing to perform a phase only correlation process on target images received sequentially. The CPU 401 specifies the content of a process to be performed by the GPU 410 in the phase only correlation process for the target images, and instructs the GPU 410 to perform the process. The result of the process is transferred from the second memory 413 to the first memory 402 under the control of the CPU 401. The target image processing is described in detail later.

(S14: Does Photographing End?)

When subject's eye to be photographed is changed, the result of the base image processing performed in step S12 becomes unnecessary. Accordingly, the CPU 401 determines whether or not the photographing of the subject's eye E subjected to tracking is completed. The CPU 401 may be configured to determine whether the photographing of the subject's eye E is completed based on, for example, the operation performed by the user on the operation unit 240B. Having determined that the photographing of the subject's eye E is not completed (S14: NO), the CPU 401 moves to step S13. On the other hand, having determined that the photographing of the subject's eye E is completed (S14: YES), the CPU 401 proceeds to step S15 to perform processing on the target image in the next frame.

(S15: Next Photographing?)

Subsequently, if the photographing of another eye is performed, the base image processing is required to be performed again. Accordingly, the CPU 401 determines whether or not to perform the next photographing of a subject's eye. Having determined not to perform the next photographing (S15: NO), the CPU 401 terminates a series of processes (END). On the other hand, having determined to perform the next photographing (S15: YES), the CPU 401 proceeds to step S12.

(Base Image Processing)

Figure 8:
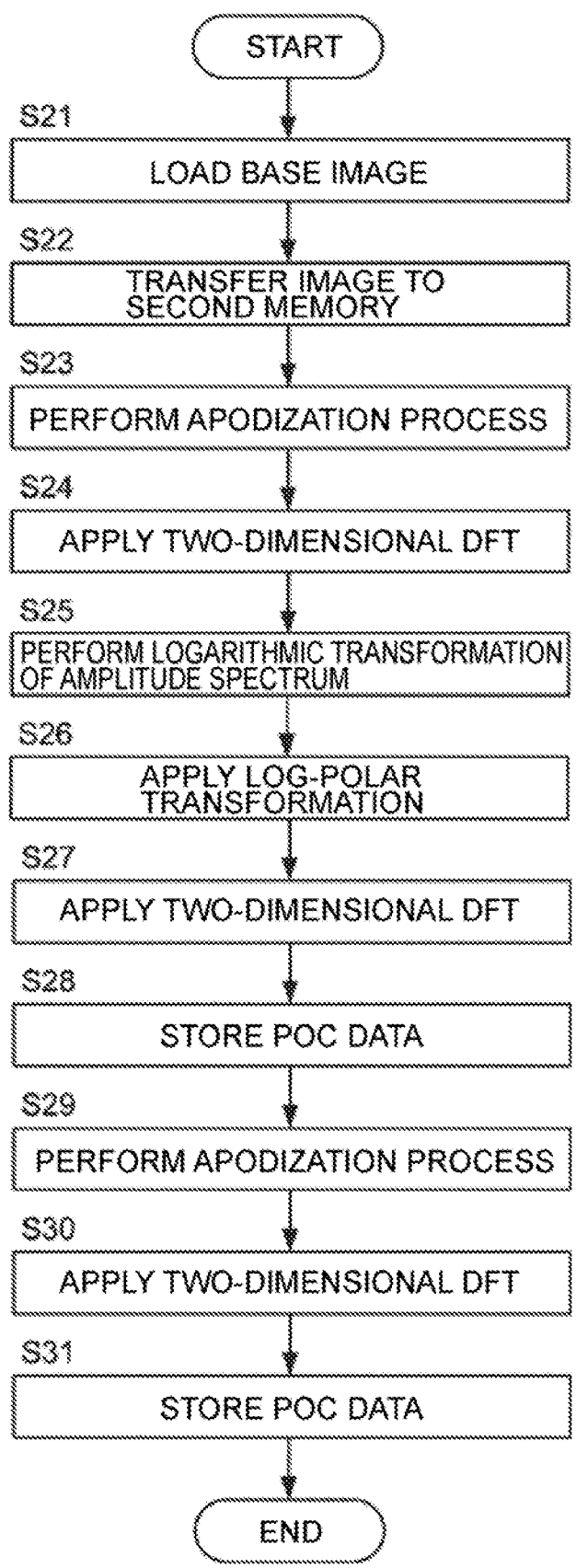
FIG. 8 is a flowchart illustrating an example of the operation of the ophthalmologic apparatus of the embodiment.

Next, a description is given in detail of the base image processing in step S12 with reference to FIGS. 8 to 13B. FIG. 8 is a flowchart illustrating the operation of the ophthalmologic apparatus. FIGS. 9 to 13B are schematic diagrams for explaining the steps of FIG. 8.

FIG. 8 illustrates an example of a flow of the base image processing according to the present embodiment. It is assumed herein that the base image is a size of 640 (x direction)×480 (y direction), and all pixels are independent from each other so that parallel processing cam be carried out. It is also assumed that, with respect to the GPU 410, 1 warp consists of 32 threads. Incidentally, a warp is a unit of threads of the same process that can be executed in parallel.

(S21: Load Base Image)

First, in response to an instruction to start tracking, the CPU 401 loads an image of the first frame of the observation image into a storage area reserved for the base image in the first memory 402. If the first memory 402 is used as a frame memory, the CPU 401 transfers the image of the first frame to the storage area reserved for the base image, for example.

(S22: Transfer Image to Second Memory)

Figure 9:
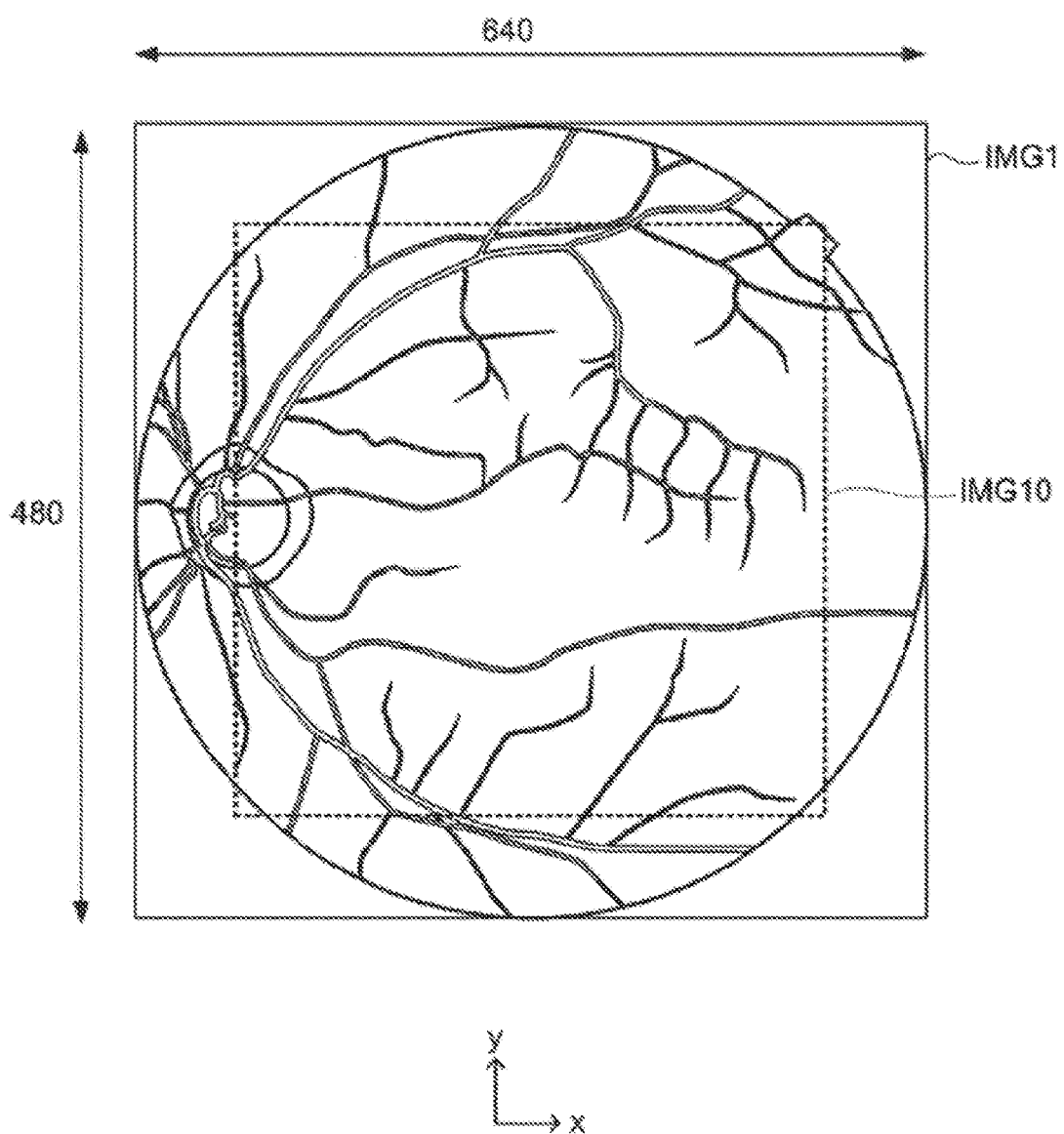
FIG. 9 is a schematic diagram for explaining an example of the operation of the ophthalmologic apparatus of the embodiment.

Subsequently, the CPU 401 clips the base image loaded into the first memory 402 (see IMG1 in FIG. 9) to a region with a size of 352×352 including the central portion (see IMG10 in FIG. 9). Incidentally, "352" is an integer multiple of the number of threads of 1 warp (in the present embodiment, "32"). The number (352) may be any integer multiple of the number of threads of 1 warp. The clipped image is stored in the first memory 402. In the following, the clipped image may sometimes be referred to as "base image". Then, the CPU 401 transfers the clipped image (base image) stored in the first memory 402 to the second memory 413. Thus, the GPU 410 is enabled to perform a specified process on the base image.

(S23: Perform Apodization Process)

Figure 10A:
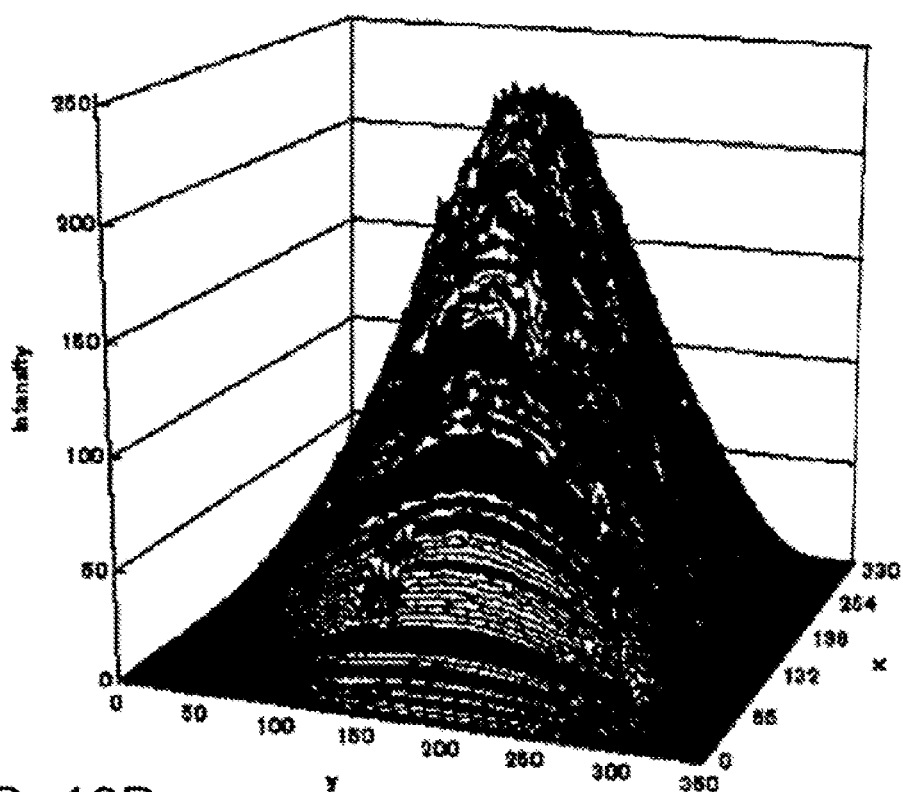
FIG. 10A is a schematic diagram for explaining an example of the operation of the ophthalmologic apparatus of the embodiment.
Figure 10B:
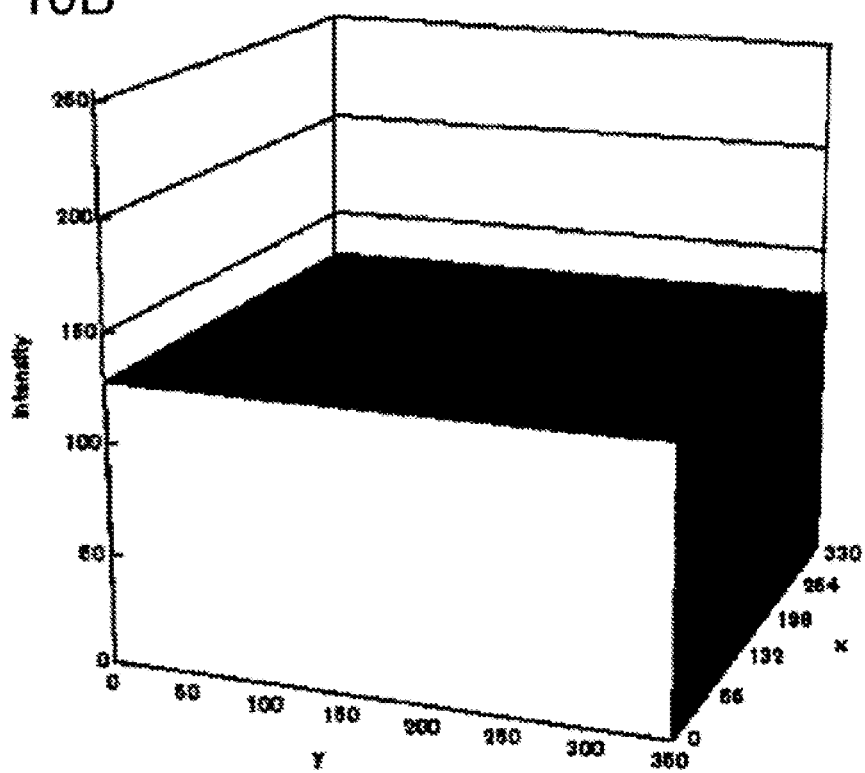
FIG. 10B is a schematic diagram for explaining an example of the operation of the ophthalmologic apparatus of the embodiment.
Figure 11:
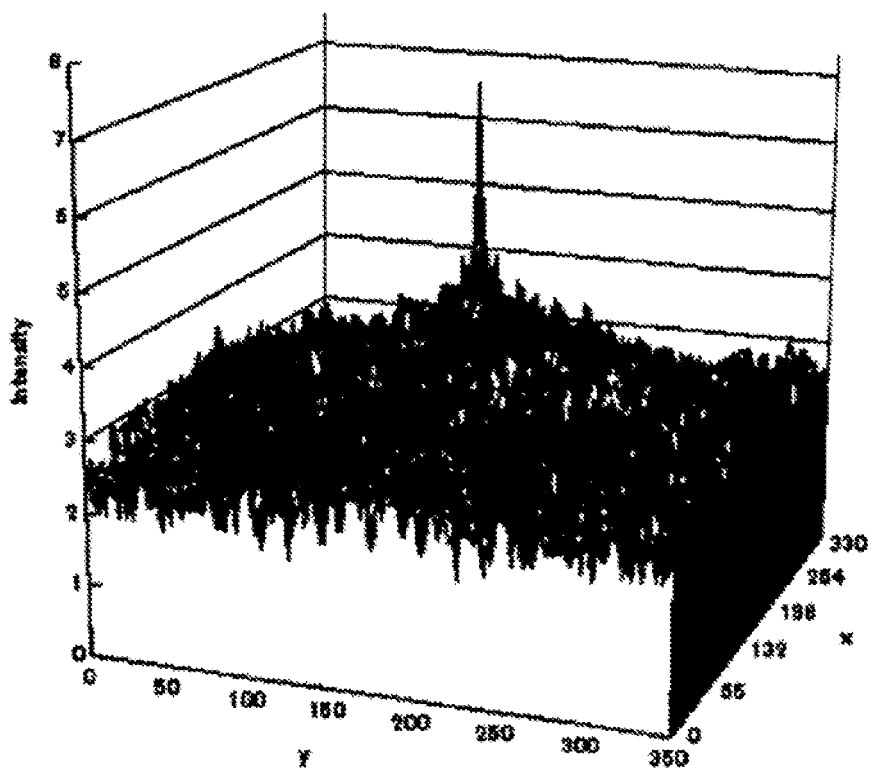
FIG. 11 is a schematic diagram for explaining an example of the operation of the ophthalmologic apparatus of the embodiment.

The GPU 410 performs an apodization process on the base image stored in the second memory 413 with the kernel function invoked by the CPU 401. The apodization process is a process to increase the dynamic range through multiplication by an apodization function to reduce the amplitude of side lobes as well as suppressing to some extent a decrease in the amplitude of the main lobe. Examples of the apodization function include window functions such as a known Hanning window, Gaussian window, rectangular window, and the like. FIG. 10A illustrates the real component of the processing result of the apodization process applied to the base image IMG10 illustrated in FIG. 9. FIG. 10B illustrates the imaginary component being biased by "128". Incidentally, in the first embodiment, the apodization process may be performed by, for example, an apodization processor (not illustrated) in the first transformation processor 301 or the rotational movement amount calculator 231.

(S24: Apply Two-Dimensional DFT)

The GPU 410 applies a two-dimensional DFT to the result of the apodization process performed on the base image (FIG. 10A, FIG. 10B) by using the kernel function. The two-dimensional DFT is the same as the process performed on the base image by the first transformation processor 301 in the first embodiment.

(S25: Perform Logarithmic Transformation of Amplitude Spectrum)

Next, the GPU 410 applies, by using the kernel function, a logarithmic transformation (see FIG. 11) to the processing result of the two-dimensional DFT. Specifically, the logarithmic transformation is represented by Equation (8) as follows:

[Equation 8]

$$Am = 20 \times \log_{10}(\sqrt{Re^2 + Im^2} + I) \qquad (8)$$

where Re is the real component of the result of the two-dimensional DFT, Im is the imaginary component thereof, and Am is the result of the logarithmic transformation. This compresses the amplitude spectrum that tends to be concentrated in the low-frequency region of spatial frequencies in a natural image. The logarithmic transformation is similar to the process performed on the base image by the logarithmic transformation unit 302 in the first embodiment.

(S26: Apply Log-Polar Transformation)

Figure 12A:
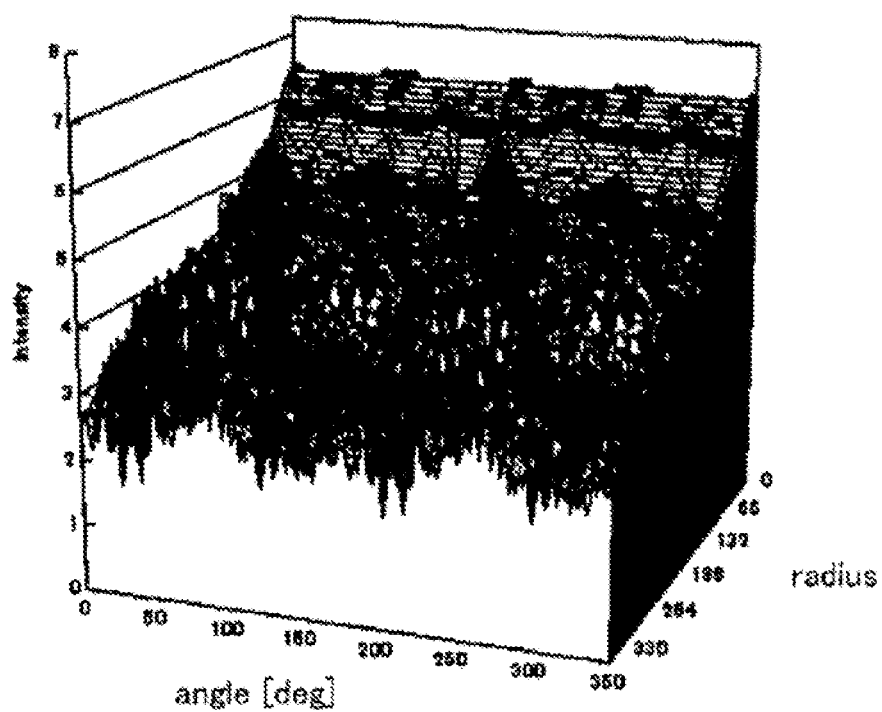
FIG. 12A is a schematic diagram for explaining an example of the operation of the ophthalmologic apparatus of the embodiment.
Figure 12B:
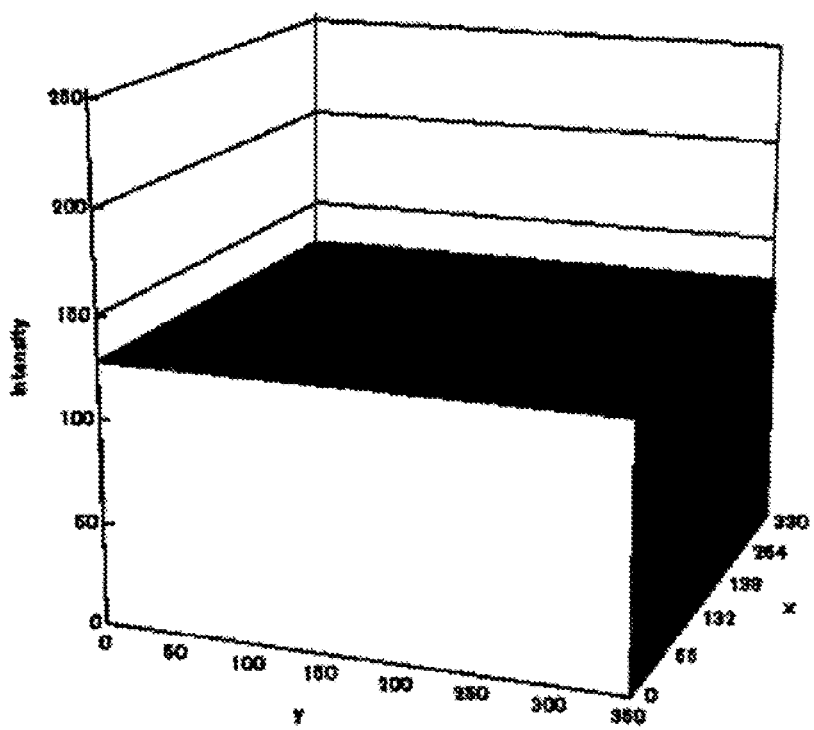
FIG. 12B is a schematic diagram for explaining an example of the operation of the ophthalmologic apparatus of the embodiment.

Next, the GPU 410 applies a Log-Polar transformation to the processing result of the logarithmic transformation by using the kernel function. Thus, the radial direction is changed to the x direction, and the argument direction is changed to the y direction. FIG. 12A illustrates the real component of the Log-Polar transformation. FIG. 12B illustrates the imaginary component being biased by "128". The Log-Polar transformation is similar to the process performed on the base image by the polar coordinate transformation unit 303 in the first embodiment.

(S27: Apply Two-Dimensional DFT)

Figure 13A:
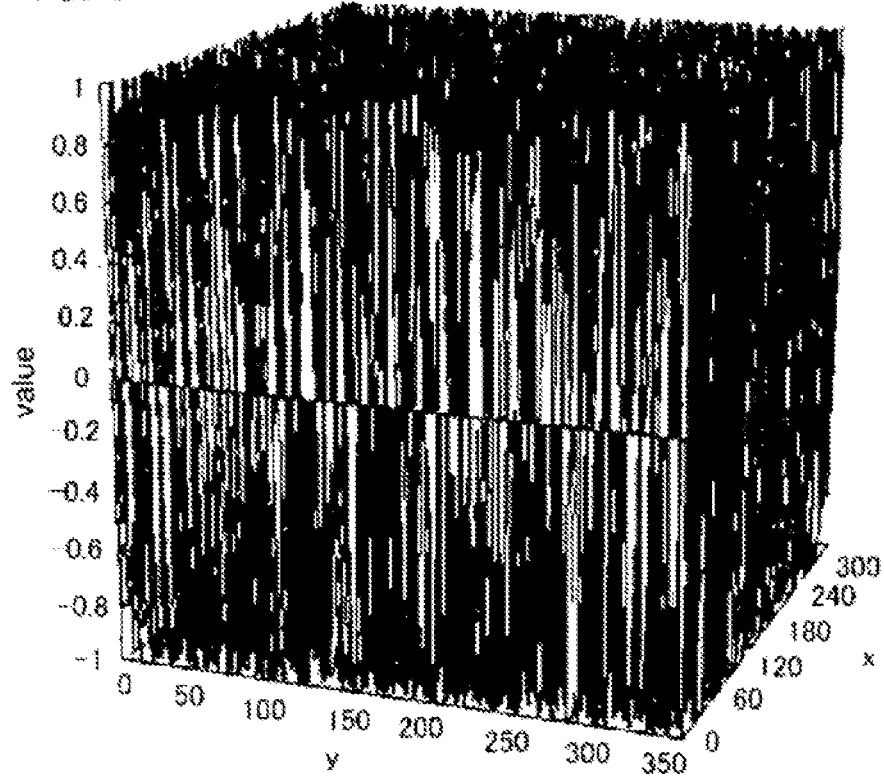
FIG. 13A is a schematic diagram for explaining an example of the operation of the ophthalmologic apparatus of the embodiment.
Figure 13B:
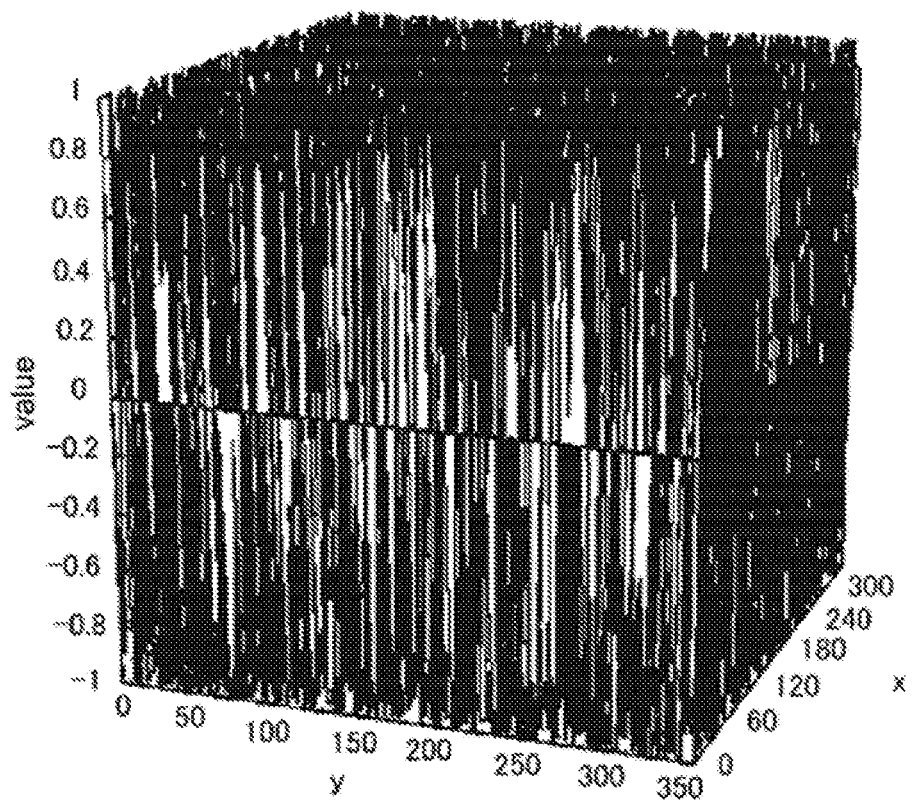
FIG. 13B is a schematic diagram for explaining an example of the operation of the ophthalmologic apparatus of the embodiment.

The GPU 410 then applies a two-dimensional DFT to the processing result of the Log-Polar transformation by using the kernel function. FIG. 13A illustrates the real component of the processing result of the two-dimensional DFT. FIG. 13B illustrates the imaginary component thereof. The two-dimensional DFT is the same as the process performed by the second transformation processor 304 for the base image in the first embodiment.

(S28: Store POC Data)

Thereafter, the GPU 410 performs normalization with the amplitude component based on the processing result of the two-dimensional DFT, and stores it in the second memory 413 as base POC data based on the processing result of the two-dimensional DFT. Here, the base POC data stored in the second memory 413 is used as the first data to calculate a correlation value of the phase only correlation function for calculating a rotational movement amount.

(S29: Perform Apodization Process)

Subsequently, the GPU 410 generates base POC data used to calculate a correlation value of the phase only correlation function for calculating parallel movement with respect to the base image. Here, the GPU 410 performs the apodization process on the base image stored in the second memory 413 with the kernel function invoked by the CPU 401. The apodization process is performed in the same manner as described for step S23. If the processing result of step S23 is stored in the second memory 413, step S29 can be dispensed with.

(S30: Apply Two-Dimensional DFT)

The GPU 410 applies a two-dimensional DFT to the real component of the result of the apodization process performed on the base image. The two-dimensional DFT is the same as the process performed on the base image by the third transformation processor 311 in the first embodiment.

(S31: Store POC Data)

Next, the GPU 410 performs normalization with the amplitude component based on the processing result of the two-dimensional DFT, and stores it in the second memory 413 as base POC data based on the processing result of the two-dimensional DFT. Here, the base POC data stored in the second memory 413 is used as the third data to calculate a correlation value of the phase only correlation function for calculating a parallel movement amount. With this, a series of processes of the base image processing is completed (END).

(Target Image Processing)

Figure 14:
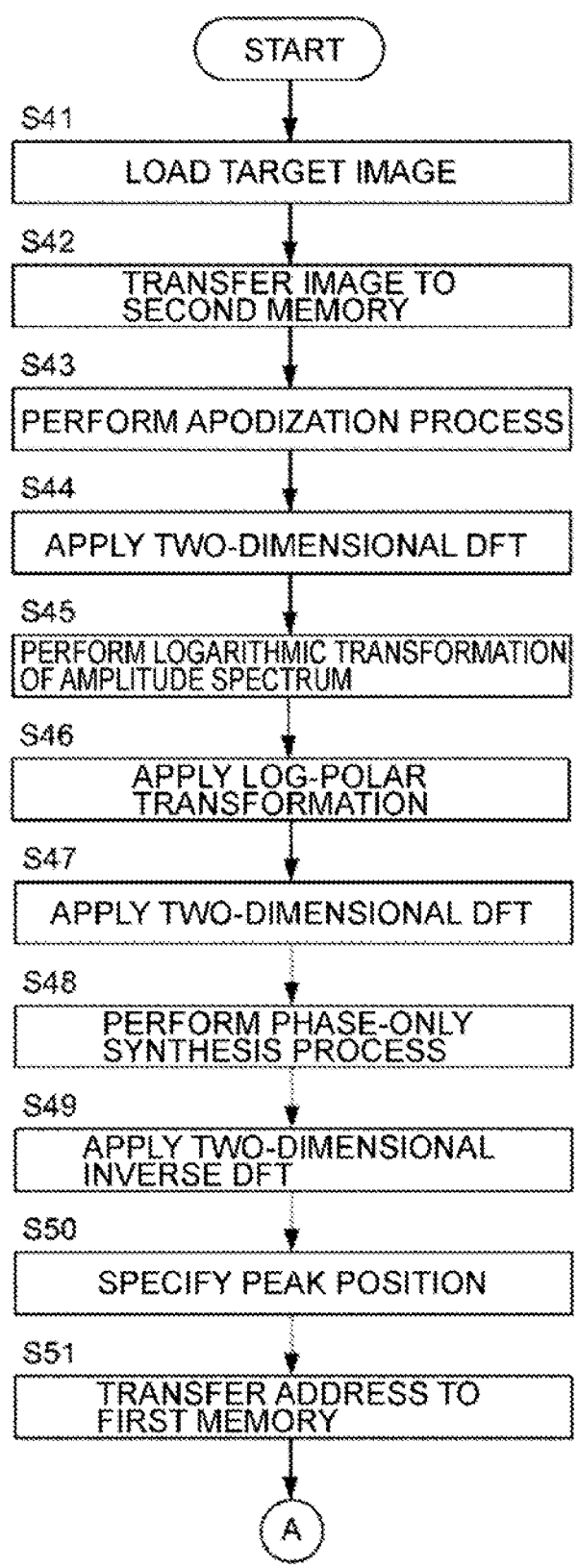
FIG. 14 is a flowchart illustrating an example of the operation of the ophthalmologic apparatus of the embodiment.
Figure 15:
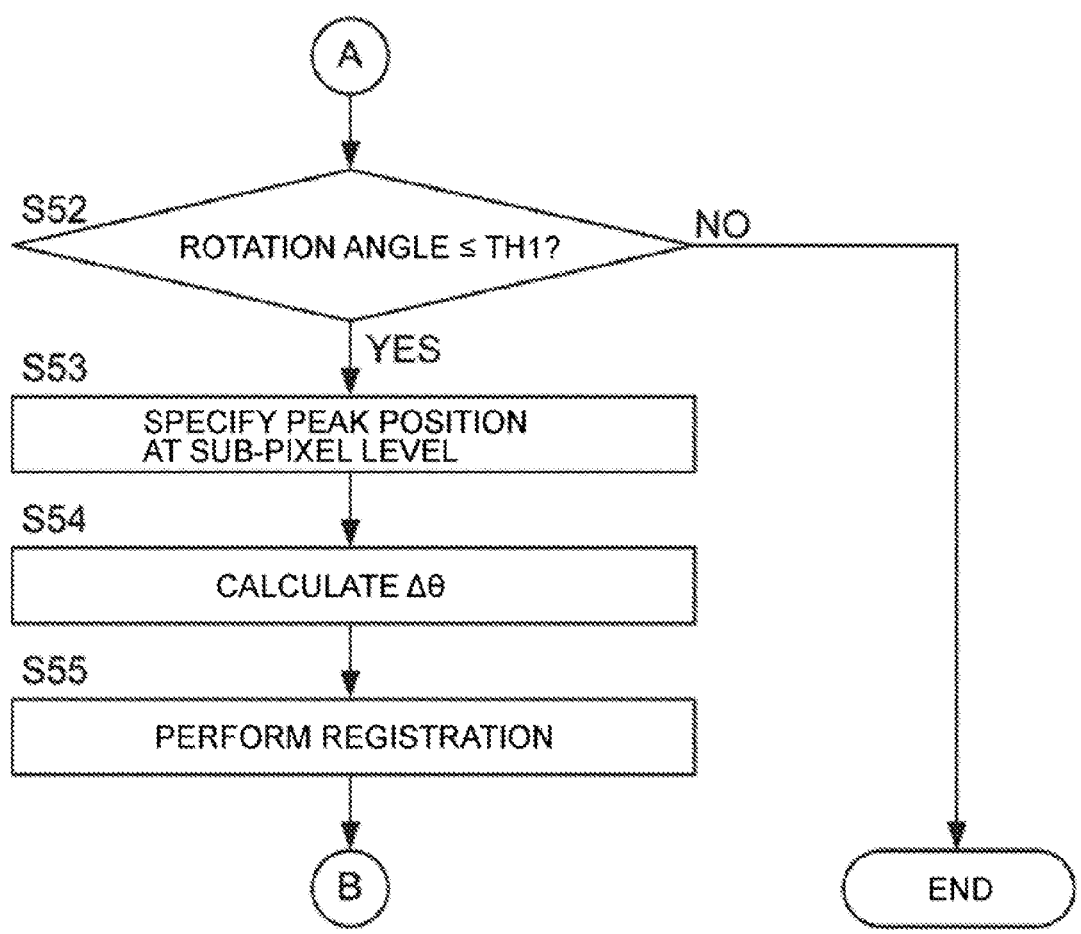
FIG. 15 is a flowchart illustrating an example of the operation of the ophthalmologic apparatus of the embodiment.
Figure 16:
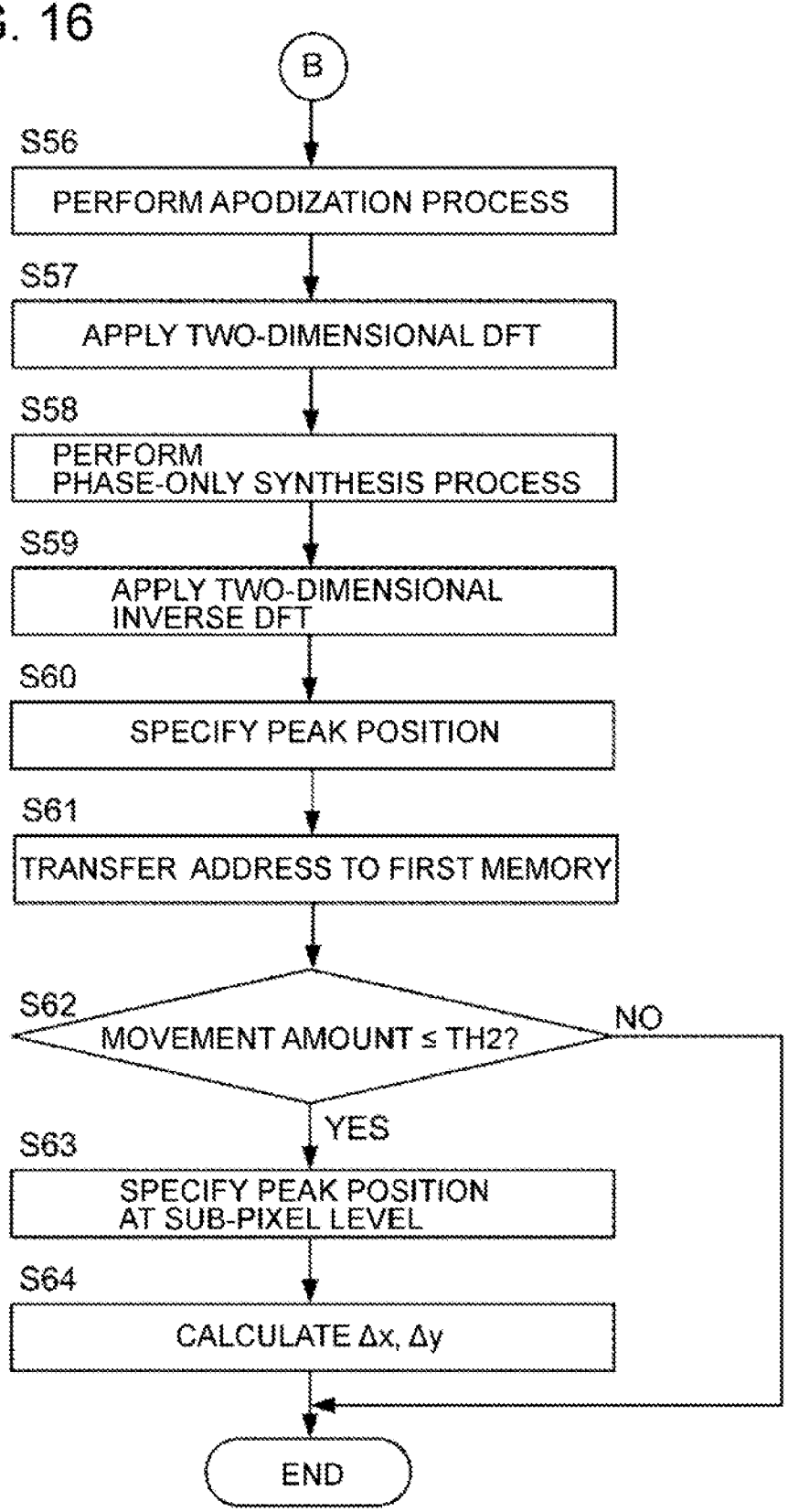
FIG. 16 is a flowchart illustrating an example of the operation of the ophthalmologic apparatus of the embodiment.

Next, a description is given in detail of the target image processing in step S13 with reference to FIGS. 14 to 21. FIGS. 14 to 16 are flowcharts illustrating the operation of the ophthalmologic apparatus. FIGS. 17 to 21 are schematic diagrams for explaining the steps of FIGS. 14 to 16.

FIGS. 14 to 16 illustrate an example of a flow of the target image processing according to the present embodiment. The target image processing includes a process of generating target POC data for the target image, a process of calculating a rotational movement amount, a registration process, and a process of calculating a parallel movement amount.

(S41: Load Target Image)

First, the CPU 401 loads an image of each of frames, which have been received sequentially, into a storage area reserved for the target image in the first memory 402. If the first memory 402 is used as a frame memory, the CPU 401 transfers the image of each frame to, for example, the storage area reserved for the target image.

(S42: Transfer Image to Second Memory)

Subsequently, the CPU 401 clips the target image stored in the first memory 402 to a region with a size of 416×416 including the central portion. Incidentally, "416" is an integer multiple of the number of threads of 1 warp, and this size (416) takes into account the rotation. That is, the size is set so as to ensure the same image size as the base image even after the target image is rotated in the rotation direction. The actual processing is performed with a size of 352×352 as in the base image processing. The size of the clipped image may be larger than "352", and it may be an integer multiple of the number of threads. The clipped image is stored in the first memory 402. In the following, the clipped image may sometimes be referred to as "target image". Then, the CPU 401 transfers the clipped image (target image) stored in the first memory 402 to the second memory 413. Thus, the GPU 410 is enabled to perform a specified process on the target image.

(S43: Perform Apodization Process)

The GPU 410 performs an apodization process on the target image stored in the second memory 413 with the kernel function invoked by the CPU 401. This process is performed in the same manner as described for step S23. In the first embodiment, the apodization process is performed by, for example, an apodization processor (not illustrated) in the first transformation processor 301 or the rotational movement amount calculator 231.

(S44: Apply Two-Dimensional DFT)

The GPU 410 applies a two-dimensional DFT to the result of the apodization process performed on the target image. The two-dimensional DFT is the same as the process performed on the target image by the first transformation processor 301 in the first embodiment.

(S45: Perform Logarithmic Transformation of Amplitude Spectrum)

Next, the GPU 410 applies, by using the kernel function, a logarithmic transformation to the processing result of the two-dimensional DFT. The logarithmic transformation is the same as that in step S25, and is the same as the process performed on the target image by the logarithmic transformation unit 302 in the first embodiment.

(S46: Apply Log-Polar Transformation)

The GPU 410 applies a Log-Polar transformation to the processing result of the logarithmic transformation by using the kernel function. The Log-Polar transformation is the same as that in step S26, and is the same as the process performed on the target image by the polar coordinate transformation unit 303 in the first embodiment.

(S47: Apply Two-Dimensional DFT)

The GPU 410 then applies a two-dimensional DFT to the processing result of the Log-Polar transformation by using the kernel function. The two-dimensional DFT is the same as the process performed on the target image by the second transformation processor 304 in the first embodiment.

(S48: Perform Phase Only Synthesis Process)

Next, the GPU 410 performs the phase only synthesis process according to Equation (3), by using a kernel function, on the base POC data stored in the second memory 413 in step S28, and on the target POC data obtained by normalizing the processing result of the two-dimensional DFT in step S47 with the amplitude component. This process is the same as the process performed by the first phase only synthesis unit 305 in the first embodiment.

(S49: Apply Two-Dimensional IDFT)

Figure 17:
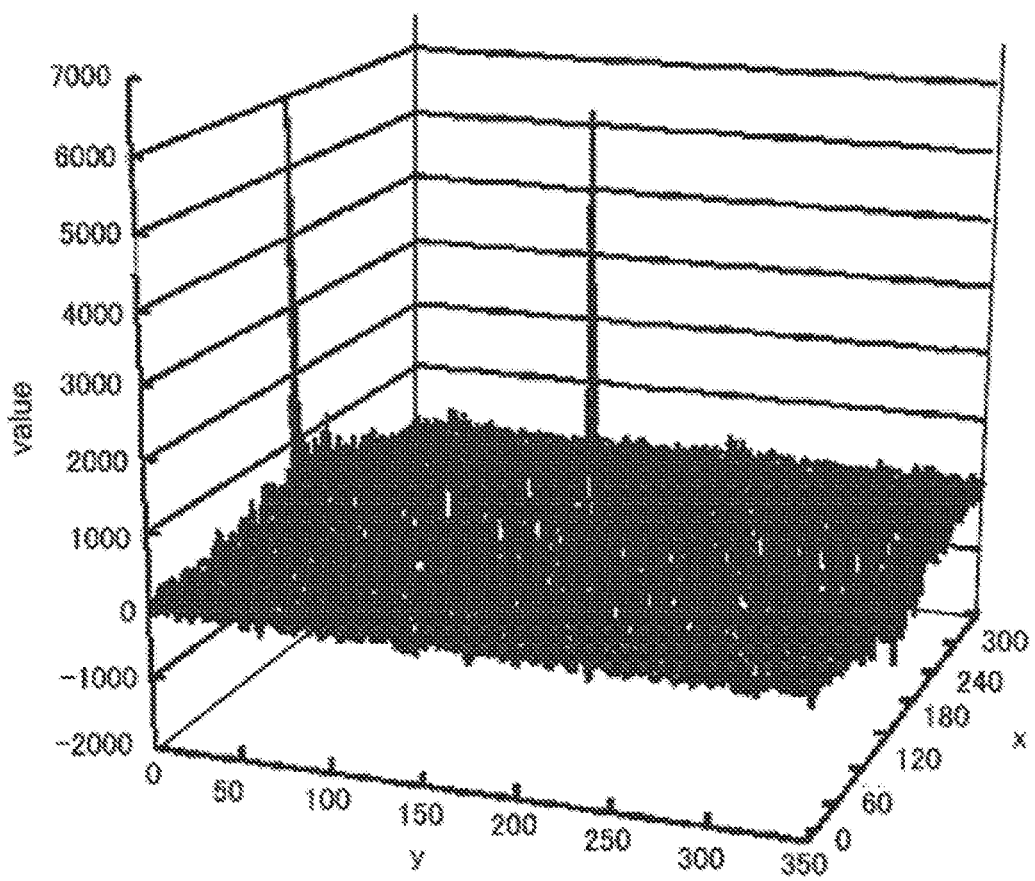
FIG. 17 is a schematic diagram for explaining an example of the operation of the ophthalmologic apparatus of the embodiment.

Thereafter, the GPU 410 applies a two-dimensional IDFT to the processing result of the phase only synthesis process according to Equation (4) by using a kernel function. FIG. 17 illustrates the real component of the processing result of the two-dimensional IDFT. This process is the same as the process performed by the first inverse transformation processor 306 in the first embodiment.

(S50: Specify Peak Position)

By specifying a peak position from the processing result of step S49 illustrated in FIG. 17, the radius vector (a coordinate in the x direction) and the argument (a coordinate in the y direction) with a high correlation value are specified at the pixel level. Accordingly, the GPU 410 obtains the peak value of the processing result in step S49 by using a kernel function. The GPU 410 also obtains the address of a peak position corresponding to the peak value, and stores it in the second memory 413.

(S51: Transfer Address to First Memory)

The CPU 401 transfers the address of the peak position stored in the second memory 413 to the first memory 402. Thereby, the CPU 401 is enabled to calculate a rotational movement amount (Δθ) at the sub-pixel level based on the address of the peak position stored in the first memory 402.

(S52: Rotation Angle≤TH1?)

The CPU 401 determines whether or not the rotation angle corresponding to the argument is not greater than the first threshold TH1 based on the address of the peak position stored in the first memory 402. Having determined that the rotation angle is greater than the first threshold TH1 (S52: NO), the CPU 401 determines it as an error, and ends a series of processes (END). Meanwhile, having determined that the rotation angle is not greater than the first threshold TH1 (S52: YES), the CPU 401 proceeds to step S53.

(S53: Specify Peak Position at Sub-Pixel Level)

When it is determined that the rotation angle is not greater than the first threshold TH1, the GPU 410 calculates a correlation value of the phase only correlation function at the sub-pixel level according to Equation (7) by using a kernel function. Specifically, in the phase only correlation function of Equation (7), the GPU 410 obtains a plurality of correlation values by changing $n_j$ (j is 1 or 2) within a range of +3 to −3, and $\delta_j$ within a range of +1 to −1, each by 0.05 step, around the pixels corresponding to the peak position as the center. That is, the GPU 410 obtains a plurality of correlation values at the sub-pixel level within a range of 3 pixels from a pixel corresponding to the peak position as the center in the $n_1$ direction (here, the x direction, the radial direction) and the $n_2$ direction (here, the y direction, the argument direction).

In this case, in the phase only correlation function represented by Equation (7), when $n_1=\delta_1=0$ or $n_2=\delta_2=0$, the denominator is zero. If the denominator is zero, exception processing for division by zero occurs in the GPU 410, which causes a reduction in the processing speed. Therefore, prior to the calculation of the correlation values, $n_1=\delta_1=0$ or $n_2=\delta_2=0$ may be checked by a branch instruction in the control syntax. However, if the arithmetic processors 412$_1$ to 412$_Q$ have threads that execute a task when the branch instruction is true as well as threads that execute a task when the branch instruction is false, branch divergence occurs. This reduces the processing speed.

Figure 18:
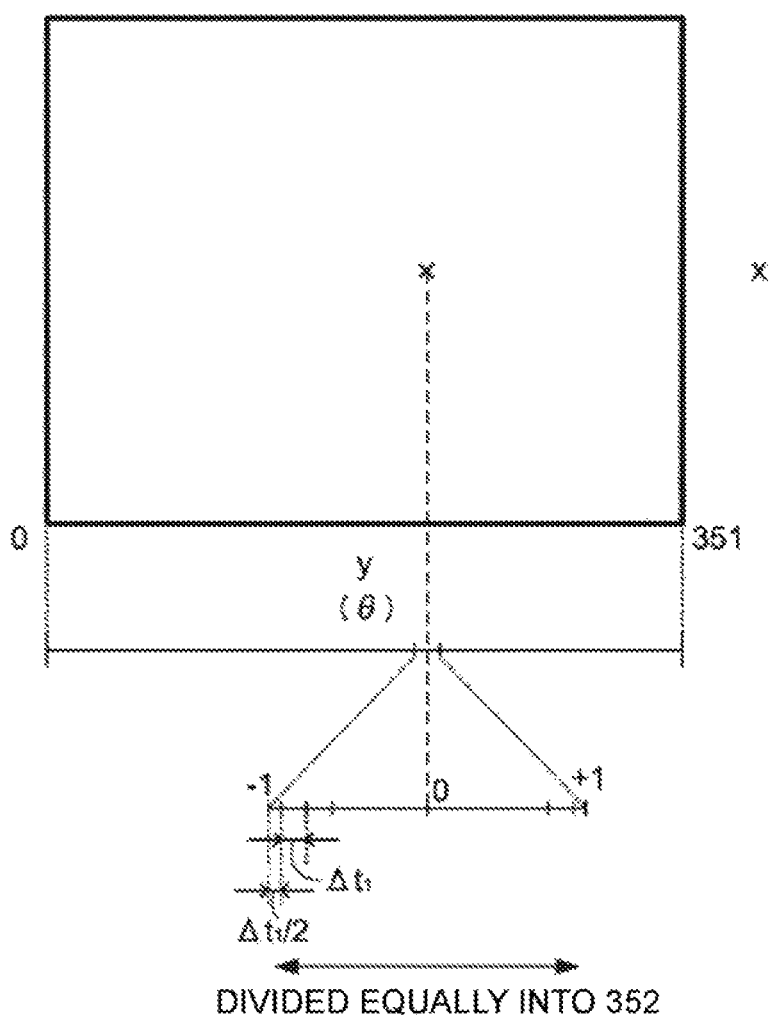
FIG. 18 is a schematic diagram for explaining an example of the operation of the ophthalmologic apparatus of the embodiment.

Therefore, in the present embodiment, $n_1$, $n_2$, $\delta_1$, and $\delta_2$ are varied such that the denominator of Equation (7) becomes a non-zero value to obtain a plurality of correlation values of the phase only correlation function represented by Equation (7). Specifically, in Equation (7), while $n_1$ and $n_2$ are varied at the pixel level in the range of +3 to −3, $\delta_1$ and $\delta_2$ are varied as illustrated in FIG. 18. Incidentally, in FIG. 18, the y direction is indicated according to the y direction in FIG. 17. That is, because the y direction (argument) of the processing result of the two-dimensional IDFT in step S49 is divided equally into 352 pieces in a range of +180° to −180°, assuming $\Delta t_1 = 2/352$ and $\delta_1$ is varied as follows in units of $\Delta t_1$:

$$\delta_1 = (-1 + \Delta t_1/2) = -0.997159$$

$$\delta_1 = (-1 + 3\Delta t_1/2) = -0.991477$$

...

$$\delta_1 = -\Delta t_1/2 = -0.002841$$

$$\delta_1 = \Delta t_1/2 = +0.002841$$

...

$$\delta_1 = (1 - 3\Delta t_1/2) = +0.991477$$

$$\delta_1 = (1 - \Delta t_1/2) = +0.997159$$

Besides, $\delta_2$ is also varied in the same manner as $\delta_1$.

As a result, the denominator of Equation (7) becomes a non-zero value. This eliminates the need to check $n_1=\delta_1=0$ or $n_2=\delta_2=0$ by a branch instruction. Accordingly, a branch instruction can be removed from the kernel function, which suppresses a decrease in the processing speed due to branch divergence. Thus, the arithmetic processors 412$_1$ to 412$_Q$ can perform the parallel processing at high speed.

In this manner, $n_1$, $n_2$, $\delta_1$, and $\delta_2$ are varied to obtain a plurality of correlation values of the phase only correlation function represented by Equation (7). Then, a peak position is specified to determine the argument (the coordinate of the y direction) with a high correlation value. The GPU 410 obtains the peak value of the correlation values of the phase only correlation function represented by Equation (7) by using a kernel function. The GPU 410 then obtains an address corresponding to the peak value, and stores it in the second memory 413.

(S54: Calculate $\Delta\theta$)

Next, the CPU 401 calculates a rotational movement amount $\Delta\theta$ corresponding to the peak position specified at the sub-pixel level.

Figure 19:
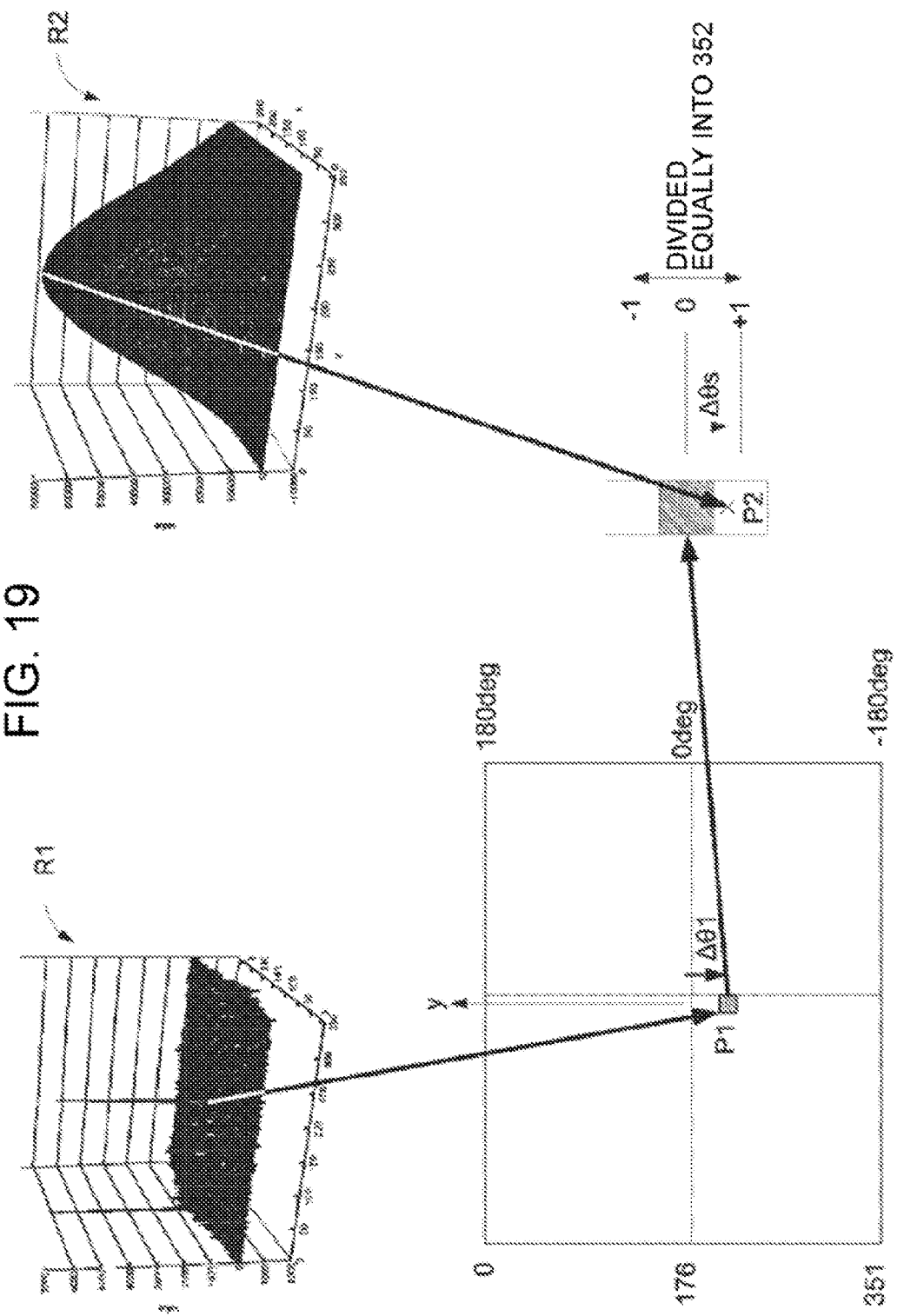
FIG. 19 is a schematic diagram for explaining an example of the operation of the ophthalmologic apparatus of the embodiment.

FIG. 19 is an explanatory diagram for step S54. FIG. 19 illustrates the relationship among the processing result R1 of the two-dimensional IDFT in step S49, the result R2 of processing of obtaining correlation values of the phase only correlation function in the vicinity of the peak position obtained in step S53, and the rotational movement amount $\Delta\theta$. The peak position P1 is specified at the pixel level from the processing result R1. In the vicinity of the peak position P1, the peak position P2 of the phase only correlation function obtained at the sub-pixel level is specified. Then, the rotational movement amount $\Delta\theta 1$ in the peak position P1, and the rotational movement amount $\Delta\theta s$ corresponding to a misregistration amount of the peak position P2 are found. Accordingly, the rotational movement amount $\Delta\theta$ is obtained as follows:

$$\Delta\theta = \Delta\theta 1 + \Delta\theta s$$

In this manner, in the GPU 410, the arithmetic processors 412$_1$ to 412$_Q$ calculate second correlation values of the second phase only correlation function in parallel while making second parameters ($n_1$, $n_2$, $\delta_1$, and $\delta_2$) different from one another. The second parameters are of the second phase only correlation function based on the base image and the target image. Then, the CPU 401 can obtain, as the rotational movement amount, a misregistration amount corresponding to a second correlation value selected from the second correlation values calculated by the arithmetic processors 412$_1$ to 412$_Q$.

(S55: Perform Registration)

When the rotational movement amount $\Delta\theta$ is calculated, the GPU 410 rotates the target image in a size of 416×416 stored in the second memory 413 by $-\Delta\theta$ by using a kernel function invoked by the CPU 401.

(S56: Perform Apodization Process)

Subsequently, the GPU 410 calculates a parallel movement amount. Specificlly, the GPU 410 performs the apodization process on the target image registered in step S55 by using a kernel function. This process is performed by an apodization processor (not illustrated) in the third transformation processor 311 or the parallel movement amount calculator 233, in the first embodiment.

(S57: Apply Two-Dimensional DFT)

The GPU 410 applies a two-dimensional DFT to the result of the apodization process performed on the target image by using the kernel function. The two-dimensional DFT is the same as the process performed on the target image by the third transformation processor 311 in the first embodiment.

(S58: Perform Phase Only Synthesis Process)

Next, the GPU 410 performs the phase only synthesis process according to Equation (3), by using a kernel function, on the base POC data stored in the second memory 413 in step S31, and on the target POC data obtained by normalizing the processing result of the two-dimensional DFT in step S57 with the amplitude component. This process is the same as the process performed by the second phase only synthesis unit 312 in the first embodiment.

(S59: Apply Two-Dimensional IDFT)

Figure 20:
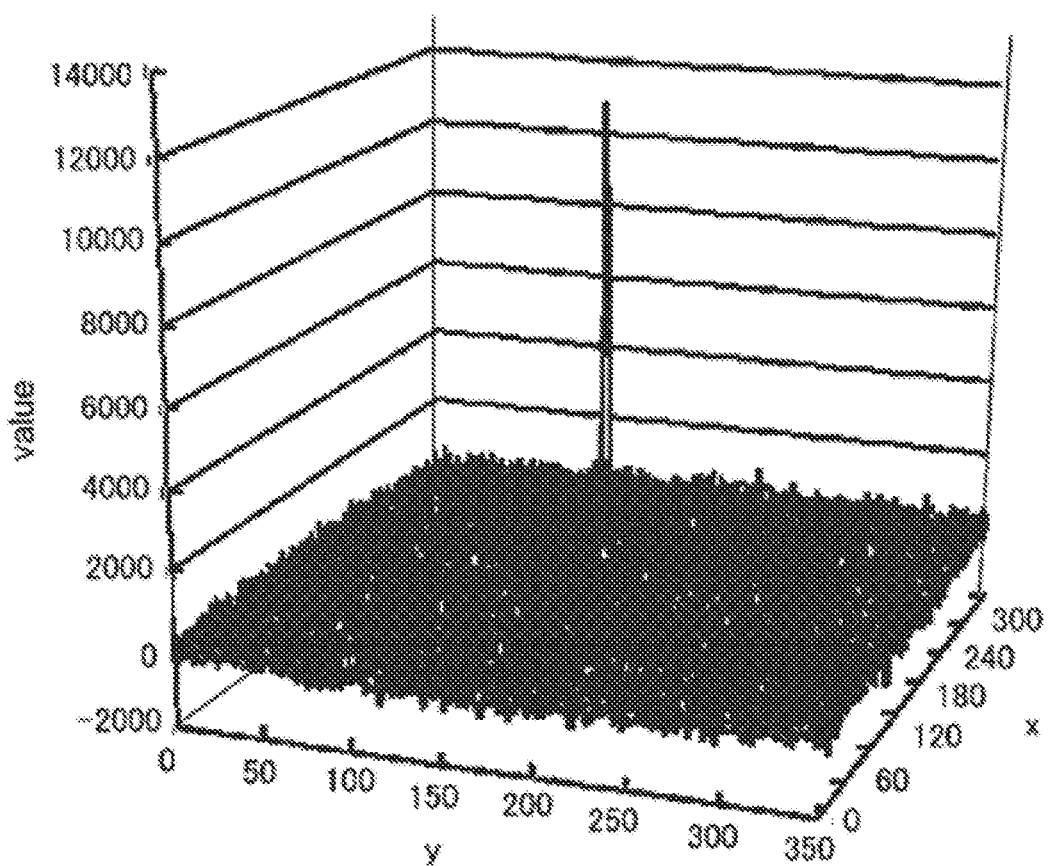
FIG. 20 is a schematic diagram for explaining an example of the operation of the ophthalmologic apparatus of the embodiment.

Thereafter, the GPU 410 applies a two-dimensional IDFT to the processing result of the phase only synthesis process according to Equation (4) by using a kernel function. FIG. 20 illustrates the real component of the processing result of the two-dimensional IDFT. This process is the same as the process performed by the second inverse transformation processor 313 in the first embodiment.

(S60: Specify Peak Position)

By specifying a peak position from the processing result of step S59 illustrated in FIG. 20, the coordinate in the x direction and the coordinate in the y direction corresponding to the correlation value are specified. The GPU 410 obtains the peak value of the processing result in step S59 by using a kernel function. The GPU 410 also obtains the address of a peak position corresponding to the peak value, and stores it in the second memory 413.

(S61: Transfer Address to First Memory)

Thereafter, the CPU 401 transfers the address of the peak position stored in the second memory 413 to the first memory 402. Thereby, the CPU 401 can calculate the parallel movement amount ($\Delta x$, $\Delta y$) at the sub-pixel level based on the address of the peak position stored in the first memory 402.

(S62: Movement Amount≤TH2?)

The CPU 401 determines whether, for example, the movement amount in the x direction and the movement amount in the y direction are not greater than the second threshold TH2 based on the address of the peak position stored in the first memory 402. Having determined that the movement amount in the x direction or the movement amount in the y direction are greater than the second threshold TH2 (S62: NO), the CPU 401 determines it as an error, and ends a series of processes (END). Meanwhile, having determined that the movement amount in the x direction and the movement amount in the y direction are not greater than the second threshold TH2 (S62: YES), the CPU 401 proceeds to step S63.

(S63: Specify Peak Position at Sub-Pixel Level)

When it is determined that the movement amount in the x direction and the movement amount in the y direction are not greater than the second threshold TH2, the GPU 410 calculates a correlation value of the phase only correlation function at the sub-pixel level according to Equation (7) by using a kernel function. Specifically, in the phase only correlation function of Equation (7), the GPU 410 obtains a plurality of correlation values by changing $n_j$ (j is 1 or 2) in a range of +3 to −3, and $\delta_j$ in a range of +1 to −1, each by 0.05 step, around the pixels corresponding to the peak position as the center. That is, the GPU 410 obtains a plurality of correlation values at the sub-pixel level in a range of 3 pixels from a pixel corresponding to the peak position as the center in the $n_1$ direction (here, the x direction) and the $n_2$ direction (here, the y direction).

In this case, as in step S53, $n_1$, $n_2$, $\delta_1$, and $\delta_2$ are varied such that the denominator of Equation (7) becomes a non-zero value to obtain a plurality of correlation values of the phase only correlation function represented by Equation (7). Specifically, in Equation (7), while $n_1$ and $n_2$ are varied at the pixel level in the range of +3 to −3, $\delta_1$ and $\delta_2$ are varied in the same manner as in step S53.

As a result, the denominator of Equation (7) becomes a non-zero value. This eliminates the need to check $n_1=\delta_1=0$ or $n_2=\delta_2=0$ by a branch instruction. Accordingly, a branch instruction can be removed from the kernel function, which suppresses a decrease in the processing speed due to branch divergence. Thus, the arithmetic processors $412_1$ to $412_Q$ can perform the parallel processing at high speed.

In this manner, $n_1$, $n_2$, $\delta_1$, and $\delta_2$ are varied to obtain a plurality of correlation values of the phase only correlation function represented by Equation (7). Then, a peak position is specified to determine a movement amount (the coordinate of the x direction, and the coordinate of the y direction) with a high correlation value. The GPU 410 obtains the peak value of the correlation values of the phase only correlation function represented by Equation (7) by using a kernel function. The GPU 410 then obtains an address corresponding to the peak value, and stores it in the second memory 413.

(S64: Calculate $\Delta x$, $\Delta y$)

Next, the CPU 401 calculates the parallel movement amount $\Delta x$ and $\Delta y$ corresponding to the peak position specified at the sub-pixel level.

Figure 21:
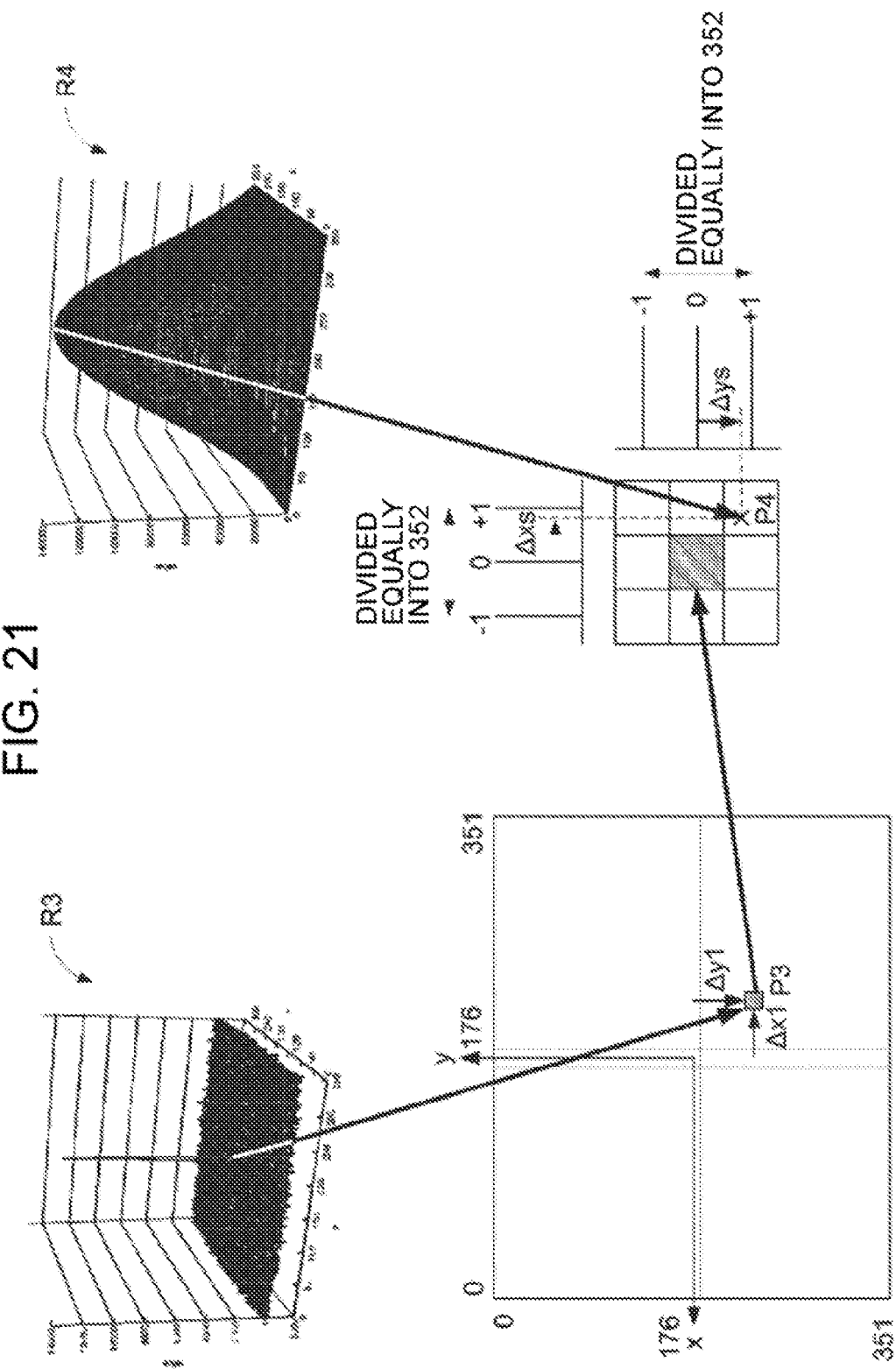
FIG. 21 is a schematic diagram for explaining an example of the operation of the ophthalmologic apparatus of the embodiment.

FIG. 21 is an explanatory diagram for step S64. In FIG. 21 illustrates the relationship among the processing result R3 of the two-dimensional IDFT in step S59, the result R4 of processing of obtaining correlation values of the phase only correlation function in the vicinity of the peak position obtained in step S63, and the parallel movement amount $\Delta x$ and $\Delta y$. The peak position P3 is specified at the pixel level from the processing result R3. In the vicinity of the peak position P3, the peak position P4 of the phase only correlation function obtained at the sub-pixel level is specified. Since the parallel movement amount $\Delta x1$ and $\Delta y1$ in the peak position P3, and the parallel movement amount Axs and Ays corresponding to a misregistration amount of the peak position P4 can be obtained, the parallel movement amount $\Delta x$ and $\Delta y$ can be calculated as follows:

$$\Delta x = \Delta x1 + \Delta xs$$

$$\Delta y = \Delta y1 + \Delta ys$$

With this, a series of processes of the target image processing is completed (END).

In this manner, in the GPU 410, the arithmetic processors $412_1$ to $412_Q$ calculate first correlation values of the first phase only correlation function in parallel while making first parameters ($n_1$, $n_2$, $\delta_1$, and $\delta_2$) different from one another. The first parameters are of the first phase only correlation function based on the base image and the target image. Then, the CPU 401 can obtain, as the parallel movement amount, a misregistration amount corresponding to a first correlation value selected from the first correlation values calculated by the arithmetic processors $412_1$ to $412_Q$.

Of the rotational movement amount $\Delta\theta$ and the parallel movement amount $\Delta x$ and $\Delta y$ calculated as above, at least the parallel movement amount $\Delta x$ and $\Delta y$ is output to the controller 210. The controller 210 (the main controller 211) controls the optical system driver 90 based on the parallel movement amount $\Delta x$ and $\Delta y$ to move the optical system provided in the fundus camera unit 2 three-dimensionally, thereby performing tracking. Note that the controller 210 (the main controller 211) may control the optical system driver 90 based on the rotational movement amount $\Delta\theta$ calculated by the image processor 230 to move (rotate) the optical system provided in the fundus camera unit 2 three-dimensionally, thereby performing tracking.

As described above, according to the present embodiment, upon obtaining a correlation value of the phase only correlation function represented by Equation (7) at the sub-pixel level, the vicinity of the peak position is shifted by $\Delta t_1/2$ for a search. This prevents the exception processing for division by zero from occurring in the arithmetic processors $412_1$ to $412_Q$ and eliminates the need of a branch instruction to check the state where the denominator becomes zero. As a result, it is possible to suppress a decrease in the processing speed due to branch divergence. Thus, the arithmetic processors $412_1$ to $412_Q$ can perform the parallel processing at high speed (e.g., processing time is reduced to ¾ under predetermined conditions).

Noted that when one pixel size of the base image and the target image is 32 micrometers×32 micrometers, a misregistration of $\Delta t_1/2$ corresponds to about 0.1 (=32×0.002841) micrometers in the parallel direction. In addition, a misregistration of $\Delta t_1/2$ corresponds to about 0.003 (=360/352× 0.002841) degree in the rotation direction. For both the parallel direction and the rotation direction, the misregistration of $\Delta t_1/2$ is no practical problem.

[Effects]

In addition to the effects of the first embodiment, the ophthalmologic apparatus of the present embodiment has the following effects.

The ophthalmologic apparatus of the embodiment may further include a plurality of arithmetic processors (e.g., the arithmetic processors $412_1$ to $412_Q$) for calculating the parallel movement amount. The arithmetic processors calculate a plurality of first correlation values of the first phase only correlation function based on the first image and the second image in parallel after making first parameters different from one another. In this case, the parallel movement amount calculator obtains a misregistration amount corresponding to a first correlation value selected from the first correlation values calculated by the arithmetic processors as the parallel movement amount.

With the ophthalmologic apparatus thus configured, a plurality of first correlation values of the first phase only correlation function can be obtained by the parallel processing of the arithmetic processors while the first parameters are made different from one another. Then, the parallel movement amount is obtained based on the first correlation value selected from these. Thus, it is possible to obtain a parallel movement amount at the sub-pixel level required to control tracking for moving images at high speed, thereby enabling high-precision tracking.

In the ophthalmologic apparatus of the embodiment, the first parameters may include a misregistration amount at the sub-pixel level. The arithmetic processors may vary the misregistration amount such that the denominator of the first phase only correlation function becomes a non-zero value to calculate the first correlation values.

With this configuration, it is possible to remove a branch instruction in the control syntax to check whether the denominator of the first phase only correlation function is zero or not. Thereby, it is possible to suppress a decrease in the processing speed due to branch divergence. Thus, arithmetic processors can perform the parallel processing at high speed.

In the ophthalmologic apparatus of the embodiment, the arithmetic processors may be configured to vary the misregistration amount at each first step (e.g., $\Delta t_1$) from a first start position (e.g., −0.997159) as a start point, which is obtained by shifting the first pixel position of the pixel level by a first misregistration amount of the sub-pixel level (e.g., $\delta_1$, $\delta_2$), in a first range (e.g., +1 to −1) (e.g., −0.997159, −0.991477, ..., −0.002841, +0.002841, ..., +0.991477, +0.997159) to calculate the first correlation values.

In the ophthalmologic apparatus of the embodiment, the first step (e.g., $\Delta t_1$) may be a double of the first misregistration amount (e.g., $\Delta t_1/2$).

With this configuration, the denominator of the first phase only correlation function can be reliably set to a non-zero value.

In the ophthalmologic apparatus of the embodiment, the arithmetic processors (e.g., the arithmetic processors $412_1$ to $412_Q$) may calculate a plurality of second correlation values of the second phase only correlation function based on the first image and the second image in parallel after making second parameters different from one another. In this case, the rotational movement amount calculator obtains a misregistration amount corresponding to a second correlation value selected from the second correlation values calculated by the arithmetic processors as the rotational movement amount.

With the ophthalmologic apparatus thus configured, a plurality of second correlation values of the second phase only correlation function can be obtained by the parallel processing of the arithmetic processors while the second parameters are made different from one another. Then, the rotational movement amount is obtained based on the second correlation value selected from these. Thus, it is possible to obtain a rotational movement amount at the sub-pixel level required to control tracking for moving images at high speed, thereby enabling high-precision tracking.

In the ophthalmologic apparatus of the embodiment, the second parameters may include a misregistration amount at the sub-pixel level. The arithmetic processors may vary the misregistration amount such that the denominator of the second phase only correlation function becomes a non-zero value to calculate the second correlation values.

With this configuration, it is possible to remove a branch instruction in the control syntax to check whether the denominator of the second phase only correlation function is zero or not. Thereby, it is possible to suppress a decrease in the processing speed due to branch divergence. Thus, arithmetic processors can perform the parallel processing at high speed.

In the ophthalmologic apparatus of the embodiment, the arithmetic processors may vary the misregistration amount at each second step (e.g., $\Delta t_1$) from a second start position (e.g., −0.997159) as a start point, which is obtained by shifting the second pixel position of the pixel level by a second misregistration amount of the sub-pixel level (e.g., $\delta_1$, $\delta_2$), in a second range (e.g., +1 to −1) to calculate the second correlation values.

In the ophthalmologic apparatus of the embodiment, the second step (e.g., $\Delta t_1$) may be a double of the second misregistration amount (e.g., $\Delta t_1/2$).

With this configuration, the denominator of the second phase only correlation function can be reliably set to a non-zero value.

[Modification]

The configurations described above are mere examples for embodying or carrying out the present invention, and therefore susceptible to several modifications and variations (omission, substitution, addition, etc.), all coming within the scope of the invention.

In the above embodiments, a detailed description is given of a specific example in which the fundus is illuminated with light in the near infrared region; however, the fundus may be illuminated with light in the visible region (e.g., green light).

In the above embodiments, a detailed description is given of a specific example in which the base image and the target image are two-dimensional images; however, they may be N-dimensional images (N is a natural number). In this case, for example, in phase only synthesis, N-dimensional DFT is applied instead of two-dimensional DFT, and also N-dimensional IDFT is applied instead of two-dimensional IDFT.

In the above embodiments, a detailed description is given of a specific example in which a rotational movement amount is calculated at the sub-pixel level, and position registration is performed based on the rotational movement amount at the sub-pixel level; however, the rotational movement amount may be calculated at the pixel level. In this case, the registration is performed based on the rotation movement amount calculated at the pixel level, and a parallel movement amount between the base image and the target image registered to each other is calculated at the sub-pixel level. Although the accuracy of registration by the registration unit 232 is lowered, it is possible to reduce the processing load for the calculation of a rotational movement amount.

In the above embodiments, while the base image is described as an image of the first frame after an instruction is issued for tracking, it may be an image of a frame after some frames from the issuance of the instruction. Besides, in the above embodiments, a detailed description is given of a specific example in which the phase only correlation process is performed on the base image and the target image that constitute a moving image; however, the base image and the target image may be a still image.

In the above embodiments, the difference in optical path length between the optical path of the signal light LS and that of the reference light LR is varied by changing the position of the optical path length changing unit 41; however, the method for changing the difference in optical path length is not limited to this. For example, a reflection mirror (reference mirror) may be arranged on the optical path of the reference light to change the optical path length of the reference light by moving the reference mirror along the traveling direction of the reference light, thereby changing the difference in optical path length. Besides, the optical path length of the signal light LS may also be changed by moving the fundus camera unit 2 and/or the OCT unit 100 relative to the subject's eye E, thereby changing the difference in optical path length. In addition, if the object to be measured is not a site of a living body, the difference in optical path length may be changed by moving the object in the depth direction (z direction).

A computer program for realizing the above embodiment may be stored in an arbitrary recording medium that is readable by a computer. Examples of the recording medium include a semiconductor memory, an optical disk, a magneto-optical disk (CD-ROM, DVD-RAM, DVD-ROM, MO, etc.), a magnetic storage medium (hard disk, floppy (registered trade mark) disk, ZIP, etc.), and the like.

The program may be sent/received through a network such as the Internet or LAN.

The invention claimed is:

1. An ophthalmologic apparatus comprising:
   an optical system configured to capture a moving image of a subject's eye;
   a rotational movement amount calculator configured to calculate a rotational movement amount between a first image and a second image included in the moving image acquired by the optical system;
   a registration unit configured to perform registration between the first image and the second image in a rotation direction based on the rotational movement amount calculated by the rotational movement amount calculator;
   a parallel movement amount calculator configured to perform a phase only correlation process on the first image and the second image registered by the registration unit to calculate a parallel movement amount between the first image and the second image;
   a driver configured to move the optical system; and
   a controller configured to control the driver based on the parallel movement amount calculated by the parallel movement amount calculator.

2. The ophthalmologic apparatus according to claim 1, wherein the rotational movement amount calculator is configured to perform a phase only correlation process on the first image and the second image to obtain the rotational movement amount therebetween.

3. The ophthalmologic apparatus according to claim 2, wherein
   the rotational movement amount calculator includes:
      a first transformation processor configured to apply a discrete Fourier transform to the second image;
      a polar coordinate transformation unit configured to apply a polar coordinate transformation to a calculation result for the second image obtained by the first transformation processor;
      a second transformation processor configured to apply a discrete Fourier transform to a calculation result for the second image obtained by the polar coordinate transformation unit;
      a first phase only synthesis unit configured to perform a phase only synthesis process to synthesize first data obtained for the first image in advance and second data obtained based on a calculation result obtained for the second image by the second transformation processor; and
      a first inverse transformation processor configured to apply an inverse discrete Fourier transform to a calculation result obtained by the first phase only synthesis unit, and
   the rotational movement amount calculator is configured to calculate the rotational movement amount based on a calculation result obtained by the first inverse transformation processor.

4. The ophthalmologic apparatus according to claim 3, wherein
   the first transformation processor is configured to apply a discrete Fourier transform to the first image,
   the polar coordinate transformation unit is configured to apply a polar coordinate transformation to a calculation result for the first image obtained by the first transformation processor, and
   the second transformation processor is configured to apply a discrete Fourier transform to a calculation result for the first image obtained by the polar coordinate transformation unit to generate the first data.

5. The ophthalmologic apparatus according to claim 1, wherein
   the parallel movement amount calculator include:
   a third transformation processor configured to apply a discrete Fourier transform to the second image, which has been registered to the first image by the registration unit;
   a second phase only synthesis unit configured to perform a phase only synthesis process to synthesize third data obtained for the first image in advance and fourth data obtained based on a calculation result obtained for the second image by the third transformation processor; and a second inverse transformation processor configured to apply an inverse discrete Fourier transform to a calculation result obtained by the second phase only synthesis unit, and the parallel movement amount calculator is configured to calculate the parallel movement amount based on a calculation result obtained by the second inverse transformation processor.

6. The ophthalmologic apparatus according to claim 5, wherein the third transformation processor is configured to apply the discrete Fourier transform to the first image, which has been registered to the first image by the registration unit, to generate the third data.

7. The ophthalmologic apparatus according to claim 1, further comprising a plurality of arithmetic processors configured to calculate first correlation values of a first phase only correlation function based on the first image and the second image, which have been registered by the registration unit, after making first parameters of the first phase only correlation function different from one another, wherein the parallel movement amount calculator is configured to obtain a misregistration amount corresponding to a first correlation value selected from the first correlation values calculated by the arithmetic processors as the parallel movement amount.

8. The ophthalmologic apparatus according to claim 7, wherein the first parameters include a misregistration amount at a sub-pixel level, and the plurality of arithmetic processors are configured to vary the misregistration amount such that denominator of the first phase only correlation function becomes a non-zero value to calculate the first correlation values.

9. The ophthalmologic apparatus according to claim 8, wherein the plurality of arithmetic processors are configured to vary the misregistration amount at each first step from a first start position as a start point, which is obtained by shifting a first pixel position by a first misregistration amount of the sub-pixel level, within a first range to calculate the first correlation values.

10. The ophthalmologic apparatus according to claim 9, wherein the first step is a double of the first misregistration amount.

11. The ophthalmologic apparatus according to claim 1, wherein the plurality of arithmetic processors are configured to calculate a plurality of second correlation values of a second phase only correlation function based on the first image and the second image after making second parameters of the second phase only correlation function different from one another, and the rotational movement amount calculator is configured to obtain a misregistration amount corresponding to a second correlation value selected from the second correlation values calculated by the arithmetic processors as the rotational movement amount.

12. The ophthalmologic apparatus according to claim 11, wherein the second parameters include a misregistration amount at the sub-pixel level, and the arithmetic processors are configured to vary the misregistration amount such that denominator of the second phase only correlation function becomes a non-zero value to calculate the second correlation values.

13. The ophthalmologic apparatus according to claim 12, wherein the plurality of arithmetic processors are configured to vary the misregistration amount at each second step from a second start position as a start point, which is obtained by shifting a second pixel position by a second misregistration amount of the sub-pixel level, within a second range to calculate the second correlation values.

14. The ophthalmologic apparatus according to claim 13, wherein the second step is a double of the second misregistration amount.

15. The ophthalmologic apparatus according to claim 1, wherein the controller is configured to control the driver based on at least one of the rotational movement amount and the parallel movement amount.

* * * * *